United States Patent
Imai et al.

(10) Patent No.: US 7,070,946 B2
(45) Date of Patent: Jul. 4, 2006

(54) BONE METABOLISM RELATED PROTEIN AND GENE THEREOF

(75) Inventors: Yuji Imai, Ashiya (JP); Hiroyuki Akatsuka, Kokubunji (JP); Eri Kawai, Otsu (JP); Kenji Omori, Saitama (JP); Noriyuki Yanaka, Higashihiroshima (JP); Naoki Sakurai, Mitaka (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 228 days.

(21) Appl. No.: 10/152,031

(22) Filed: May 22, 2002

(65) Prior Publication Data

US 2003/0044825 A1    Mar. 6, 2003

Related U.S. Application Data

(60) Provisional application No. 60/292,318, filed on May 22, 2001.

(51) Int. Cl.
  *G01N 33/53* (2006.01)
  *C12N 15/00* (2006.01)
  *C12N 5/00* (2006.01)
  *C07K 14/51* (2006.01)
  *C07H 21/00* (2006.01)

(52) U.S. Cl. .................. 435/7.8; 435/69.1; 435/320.1; 435/325; 435/375; 435/377; 530/399; 536/23.51

(58) Field of Classification Search ............... 435/69.1, 435/7.2, 325, 375, 320.1; 530/350
See application file for complete search history.

(56) References Cited

U.S. PATENT DOCUMENTS 5,194,596 A * 3/1993 Tischer et al. ............... 530/399

FOREIGN PATENT DOCUMENTS

JP    2000-139467    5/2000
WO    WO 01/12662    2/2001

OTHER PUBLICATIONS

Wells, Additivity of Mutational Effects in Proteins. Biochemistry 29:8509-8517 (1990).*
Karp, What we do not know about sequence analysis and sequence databases. Bioinformatics 14:753-754 (1998).*

* cited by examiner

*Primary Examiner*—Joseph J. Murphy
*Assistant Examiner*—Regina M. DeBerry
(74) *Attorney, Agent, or Firm*—Birch Stewart Kolasch & Birch LLP

(57) ABSTRACT

The present invention is directed to a novel method of detecting a function or activity of a polypeptide which is related to bone metabolism, in particular, differentiation (maturation) of osteoblast or morphological change (retraction), specifically relating to a polypeptide which comprises an amino acid sequence shown by SEQ ID NO: 2 or SEQ ID NO: 4, an amino acid sequence in which one or several amino acids are deleted, substituted or added in the amino acid sequence shown by SEQ ID NO: 2 or SEQ ID NO: 4, or a polypeptide encoded by a nucleic acid which is capable of hybridizing under stringent condition with a nucleic acid comprising a nucleotide sequence shown by SEQ ID NO: 1 or SEQ ID NO: 3, or a complement sequence thereof.

11 Claims, 5 Drawing Sheets

Number of days cultured

Fig. 6

```
mOBDPF  228  VGHRGAPMLAPENTLMSLRKTAECGAAVFETDVMVSSDGVPFLMHDERLSRTTN  281
ecUGPQ   10  VAHRGGGKLAPENTLASIDVGAKYGHKMIEFDAKLSKDGEIFLLHDDNLERTSN   63
ecGLPQ   34  IAHRGASGYLPEHTLPAKAMAYAQGADYLEQDLVMTKDDNLVVLHDHYLDRVTD   87
hiGLPQ   38  IAHRGASGYLPEHTLESKALAFAQHSDYLEQDLAMTKDGRLVVIHDHFLDGLTD   91
```

US 7,070,946 B2

BONE METABOLISM RELATED PROTEIN AND GENE THEREOF

This application claims priority on provisional Application No. 60/292,318 filed on May 22, 2001, the entire contents of which are hereby incorporated by reference.

BACKGROUND OF THE INVENTION

1. Field of the Invention

The present invention relates to a novel protein and a gene thereof which is involved in bone metabolism. Further, the present invention relates to a novel protein and the gene thereof having a function or an activity of (i) promoting differentiation of osteoblast, (ii) inducing morphological change of a cell or (iii) an esterase activity, etc.

2. Prior Art

Normal bone metabolism depends on a balance between bone formation and born resorption. It has been known that bone formation is mainly led by osteoblast that is differentiated from a messenchymal stem cell and bone resorption is led by osteoclast that is differentiated from a hematopoietic stem cell.

It is thought that osteoporosis is caused when this balance is shifted to the bone resorption side. Osteoporosis is classified into two types. One is called postmenoposal osteoporosis in which remarkable decrease in bone mass is observed. In this type, bone metabolism is at a high turnover rate, and bone formation and bone resorption are both active. However, the balance is shifted toward the bone resorption side, thereby causing osteoporosis. The other type is called a senile osteoporosis in which a decrease in bone mass is caused gradually. In this type, a cause is thought to be a dysfunction of the osteoblast, which leads to a declined balance toward the bone resorption side.

There have been many points that are left unclear about mechanisms of the bone formation or of differentiation of osteoblasts, for example, as a factor that is involved in differentiation of osteoblasts, only a few have been known, such as bone morphogenetic protein (BMP) (Maiti, et al., Indian J. Exp. Biol., vol. 36, pp. 237 to 244, 1998), a transcription factor Cbfal (Komori, et al., Cell, vol. 89, pp. 755 to 764, 1997), etc.

On bone remodeling, there have been known facts as follows. That is, when a concentration of calcium ion in blood is lowered, secretion of parathyroid hormone (PTH) from accessory thyroid gland is increased, and PTH directly acts on bone, causing bone resorption and calcium ion release. In this process, it is known that PTH acts on osteoblasts and induces morphological change of the cells. There is a hypothesis advocating that a part of a bone surface covered by osteoblasts is exposed due to such morphological change of the osteoblasts, thereby providing a space for osteoclasts to adhere to (Rodan et al., Calcit. Tissue Int., vol. 33, pp. 349 to 351, 1981; "Principles of Bone Biology" (J. P. Bilezikian, L. G. Raisz, G. A. Rodan, eds.), 1996, Academic Press Inc., USA.). At an initial stage of bone resorption of bone remodeling, adhesion of osteoclasts to the bone surface is of importance, and, morphological change of osteoblasts is also as important. Despite of this, there has not been known much about a detailed mechanism of morphological change of osteoblasts during bone remodeling.

It has been earnestly desired that these mechanisms are solved for research and development of a therapeutic treatment method and a therapeutic agent for diseases related to bone metabolism, such as osteoporosis, etc.

SUMMARY OF THE INVENTION

An object of the present invention is to provide a novel protein and a novel gene which relate to bone metabolism. Another object of the present invention is to provide a means for detecting these functions or expressions. Still further object of the present invention other than the above will be clarified by the following descriptions.

The present inventors have found a novel protein and its gene which is specifically expressed when osteoblast-like cells (mouse MC3T3-E1) differentiate (mature) to osteoblasts having an active bone morphogenetic potential. Moreover, they have found that differentiation (maturation) to osteoblasts is promoted by overexpression of this gene in the osteoblast-like cells, and that morphological change of the cells occurs thereby, etc., and then, they have accomplished the present invention.

That is, the present invention relates to a polypeptide which comprises a polypeptide selected from the following (A), (B) and (C), and has a function or an activity selected from the following (i), (ii) and (iii):

(A) a polypeptide comprising an amino acid sequence shown by SEQ ID NO: 2 or SEQ ID NO: 4,
(B) a polypeptide comprising an amino acid sequence in which one or several amino acids are deleted, substituted or added in the amino acid sequence shown by SEQ ID NO: 2 or SEQ ID NO: 4,
(C) a polypeptide encoded by a nucleic acid which are capable of hybridizing under stringent condition with a nucleic acid comprising a nucleotide sequence shown by SEQ ID NO: 1 or SEQ ID NO: 3 or a complement sequence thereof,
(i) promoting differentiation (maturation) of osteoblast,
(ii) inducing morphological change (particularly retraction of osteoblast) of a cell, and
(iii) an esterase activity (particularly a glycerophosphodiester phosphodiesterase activity or the like).

Also, the present invention relates to a nucleic acid which encodes the above-mentioned polypeptide.

Moreover, the present invention relates to a recombinant vector and a host cell containing the same. Furthermore, the present invention relates to a method of detecting a function or an activity of the polypeptide or the nucleic acids by using the above-mentioned polypeptide or the nucleic acids. Additionally, the present invention relates to a method for screening or identifying a compound that shows an effect of modulating a function or an activity (or an expression) of the polypeptides (or the nucleic acids), using the same.

BRIEF DESCRIPTION OF THE DRAWINGS

FIG. 6 is a drawing showing homologies in amino acid sequence of OBDPF and known enzymes, SEQ ID NOS: 13–16.

DESCRIPTION OF THE PREFERRED EMBODIMENTS

Figure 1:
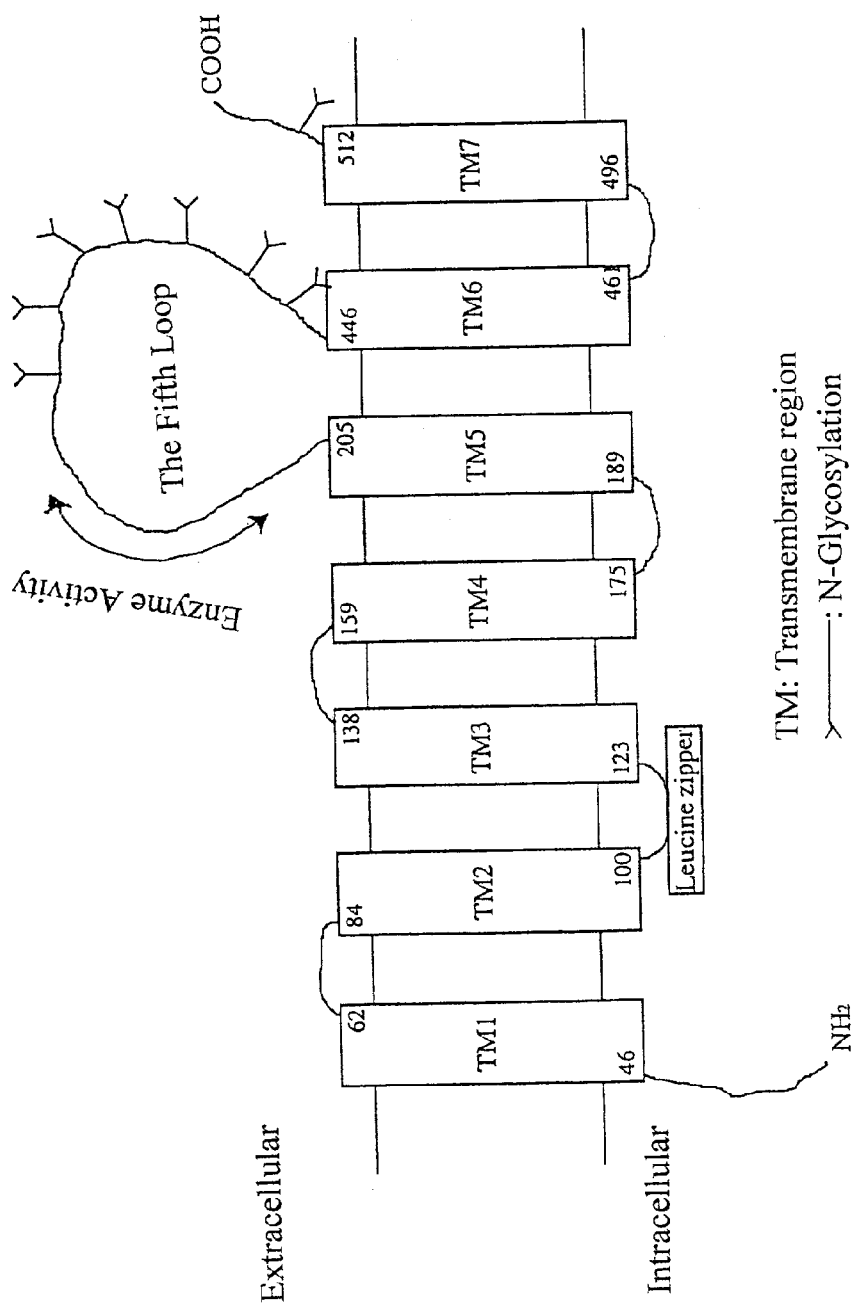
FIG. 1 is an illustration showing a predicted structure of OBDPF protein as a transmembrane protein.

Osteoblasts are cells that are responsible for bone formation, and generally exist on a forming surface of a bone that undergoes growth.

The protein (Osteoblast Differentiation Promoting Factor: OBDPF) and the gene thereof (Osteoblast Differentiation Promoting Factor gene: OBDPF gene) found by the present inventors are expressed specifically in a stage where osteoblasts undergo differentiation (maturation). That is, there is no expression or a low level of expression of the OBDPF or a gene thereof observed when osteoblasts are in undifferentiated (immature) state (a state where they do not have an active bone morphogenetic potential), but there is a higher level of expression observed when osteoblasts are in differentiation (matured) state (a state where they acquire an active bone morphogenetic potential) than in undifferentiated (immature) state.

The OBDPF protein and the gene thereof have a function to promote differentiation (maturation) of osteoblasts. That is, expression thereof promotes transferring those cells from an undifferentiated (immature) state to a differentiated (matured) state.

Further, OBDPF protein and the gene thereof have a function to induce morphological change of the cell (specifically, retraction of osteoblasts). That is, intracellular expression thereof changes a shape of the cell more spherical.

In addition, OBDPF protein has an enzyme activity (an esterase activity, in more detail, glycerophosphodiester phosphodiesterase activity).

SEQ ID NO: 1 of the sequence listing mentioned below is a nucleotide sequence of a cDNA of a mouse OBDPF gene isolated by the present inventors, and SEQ ID NO: 2 is an amino acid sequence of an OBDPF protein encoded in the coding region thereof, respectively. SEQ ID NO: 3 is a nucleotide sequence of a cDNA of a human OBDPF gene, and SEQ ID NO: 4 is an amino acid sequence of an OBDPF protein encoded in the coding region thereof, respectively. When comparison is made between amino acid sequences (539 amino acid residues) of human and mouse OBDPF proteins, there is about 87% of homology.

SEQ ID NO: 5 to 12 show a DNA sequence containing exon-intron boundary region in a genomic DNA of the mouse OBDPF.

As a protein or a polypeptide of the present invention, there may be mentioned those with an amino acid sequence shown by SEQ ID NO: 2 or NO: 4, and those with an amino acid sequence in which one or several amino acids are deleted, substituted or added in the amino acid sequence shown by SEQ ID NO: 2 or NO: 4. Deletion, substitution or addition of the amino acids may be allowed to be of such a degree that a function or an activity thereof is not lost (for example, a function to promote differentiation of osteoblasts, a function to induce morphological change of a cell and or an esterase activity), and it is generally 1 to about 110 amino acids, preferably 1 to about 55 amino acids, more preferably 1 to about 30 amino acids.

Such a protein or a polypeptide has a homology in an amino acid level of generally about 80% or more, preferably about 90% or more, more preferably about 95% or more to the amino acid sequence shown by SEQ ID NO: 2 or NO: 4. Such a protein or a polypeptide includes an artificially modified mutant protein, proteins originated from other living organisms and the like, in addition to a mutant protein discovered in nature.

These proteins or polypeptides are exemplified by a polypeptide comprising an amino acid sequence having one or more conservative amino acid substitutions in comparison with the amino acid sequences shown by SEQ ID NO: 2 or NO: 4, and this includes conservative substitution variants and naturally occurring allelic variants of the polypeptide having an amino acid sequence shown by SEQ ID NO: 2 or NO: 4.

As the gene or the nucleic acid of the present invention, there may be mentioned a nucleic acid having a nucleotide sequence shown by SEQ ID NO: 1 or NO: 3. Further, there may be mentioned a nucleic acid which is capable of hybridizing under stringent condition with a nucleic acid having a nucleotide sequence shown by SEQ ID NO: 1 or NO: 3. Such a nucleic acid that is capable of hybridizing may be any as long as functions (for example, a function to promote differentiation of osteoblasts, a function to induce morphological change of a cell, a function to express esterase activity, and the like) thereof are not lost. Such a nucleic acid has a homology of generally about 70% or more, preferably about 80% or more, more preferably about 90% or more to the nucleotide sequence shown by SEQ ID NO: 1 or NO: 3. Such a gene or a nucleic acid includes a mutant protein discovered in nature, an artificially modified mutant gene, homologous genes originated from other living organisms, etc., and nucleic acids derived therefrom.

As the protein or the polypeptide in the present invention, there may be mentioned those which are recombinant type or those which are isolated.

As the nucleic acid in the present invention, there may be mentioned a DNA molecule and an RNA molecule, and included are those which are recombinant type or those which are isolated. Further, these nucleic acids include a single stranded or double stranded nucleic acid. More specifically, for example, the nucleic acid comprising a nucleotide sequence shown by SEQ ID NO: 1 (or NO: 3) includes a single stranded DNA having said nucleotide sequence, a double stranded DNA comprising the single stranded DNA having said nucleotide sequence and the complement thereof, RNA molecules corresponding thereto, etc.

In the present invention, hybridization under stringent condition can be generally carried out by conducting hybridization for 16 hours in 6×SSC or a hybridization solution having an equivalent salt concentration at a temperature of 50 to 60° C., followed by preliminary washing with 6×SSC or a solution having an equivalent salt concentration as necessary, and subsequently washing with 1×SSC or a solution having an equivalent salt concentration. Further, under a condition with a higher stringency (high stringent condition), washing is carried out with 0.1×SSC or a solution with an equivalent salt concentration to conduct hybridization.

The gene or the nucleic acid of the present invention can be isolated and obtained by screening, using osteoblasts of mammals as a genetic source. As mammals, there maybe mentioned a non-human animals such as dog, cow, horse, goat, sheep, ape, pig, rabbit, rat and mouse, as well as human.

As osteoblasts, for example, osteoblasts isolated from bone (calvaria, etc.) of mammal as mentioned above can be used. Also, a cell line of osteoblast-like cells such as mouse osteoblast-like cell line MC3T3-E1 (Sudo, H. et al., Journal of Cell Biology, vol. 96, pp. 191–198, 1983; RIKEN RCB No.1126) can be used as osteoblasts. Or else, it is possible to use a cell which is able to be differentiated into osteoblast, example of which includes human osteosarcoma Saos-2 (RIKEN RCB No.0428) and the like.

The gene or the nucleic acid of the present invention can be isolated using a technique of selectively screening differentially expressed genes, such as a differential display method, a subtraction method, a differential hybridization method, etc., together with a differentiation model of osteoblasts. As the differentiation model of osteoblasts, in vitro culture system of osteoblasts as mentioned below can be employed.

For example, the osteoblast-like cells (mouse osteoblast-like cell line MC3T3-E1, etc.) are cultured in the presence of stimulating agent such as ascorbic acid and β-glycerol phosphate, etc., in order to induce differentiation thereby obtaining differentiated (matured) osteoblasts. Using mRNAs prepared from them, differentially expressed genes, whose expression amount differs between cells before differentiation (maturation) and those after differentiation (maturation), are screened by a method such as differential display method (Science, vol. 257, pp. 967–971, 1992 and Cancer Research, vol. 52, pp. 6966–6968, 1992) to obtain cDNA.

Using the obtained cDNA as a probe, cDNA library is screened by suitably combining a colony hybridization method, a plaque hybridization method and others to obtain entire length of cDNA. Further, by screening a genomic DNA library, genomic DNA (gene) can be isolated. In addition, homologous genes of other species of living organisms can be isolated by screening DNA libraries of other species of mammals. As such mammals, there may be mentioned a non-human animals such as dog, cow, horse, goat, sheep, ape, pig, rabbit, rat and mouse, as well as human.

Also, the gene or the nucleic acid of the present invention can be easily obtained using sequence information disclosed in the present specification (SEQ ID NO: 1 to 12 in the sequence listing shown below). For example, based on the information of the disclosed nucleotide sequence, a primer and a probe are designed and a DNA library is screened by suitably combining a PCR (polymerase chain reaction) method, a colony hybridization method, a plaque hybridization method and the like, thereby obtaining the gene or the nucleic acid of the present invention. DNA library such as cDNA library, genomic DNA library, etc., can be prepared by a method described in, for example, "Molecular cloning" (written by Sambrook, J., Fritsch, E. F. and Maniatis, T., published by Cold Spring Harbor Laboratory Press, 1989). In addition, if there is a commercially available library, it may be also used.

By determining nucleotide sequence of the obtained cDNA, the coding region encoding a protein that is a gene product can be determined, and an amino acid sequence of the protein can be obtained.

Moreover, using cDNA as a probe, northern blotting can be conducted with respect to mRNAs of undifferentiated cells and differentiated cells to confirm that the gene or the nucleic acid of the present invention is specifically expressed in a differentiation stage of osteoblasts.

A function of the protein or the polypeptide (or the gene or the nucleic acid) of the present invention can be detected as mentioned below.

i) A function of Promoting Differentiation (Maturation) of Osteoblast

For example, an expression vector to express the protein or the polypeptide (or the gene or the nucleic acid) of the present invention is introduced into undifferentiated (immatured) osteoblast and the gene is overexpressed. The overexpressed cells are cultured and a marker indicating differentiation of osteoblast is detected and measured to analyze a state of differentiation (maturation).

Osteoblasts with an active bone morphogenetic potential, namely, differentiated (matured) osteoblasts are recognized by an intracellular bone matrix deposit (deposited calcium), and they undergo calcification. Also, there exist granules exhibiting an alkaliphosphatase activity in the cytoplasm. When an active bone formation stops, it is known that those granules in osteoblasts disappear and alkaliphosphatase activity is suddenly lowered.

Therefore, as a marker for differentiation, an amount of calcification or an alkali phosphatase activity is properly used. In addition, osteocalcin activity or an amount of expression of osteopontin can be also used as a differentiation marker.

As osteoblasts, osteoblasts separated from calvaria of mammal or osteoblast-like cells (mouse osteoblast-like cell line MC3T3-E1, etc.) may be used, among which osteoblast-like cells (mouse osteoblast-like cell line MC3T3-E1, etc.) are especially preferably used.

ii) A Function of Inducing Morphological Change of Cells

For example, an expression vector designed for expressing the protein or the polypeptide (or the gene or the nucleic acid) of the present invention is introduced into cells (osteoblasts and the like) and expressed. These cells are cultured and observed with respect to morphological change (retraction). If the shape of the cell becomes spherical (retract), it is confirmed that it has a function of inducing morphological change.

iii) An Esterase Activity

For example, an enzyme activity is measured using cells in which the protein or the polypeptide of the present invention is expressed. Or else, the protein or the polypeptide may be used for the measurement of the enzyme activity after being isolated.

Since the fifth loop of the protein that is an extracellular region is responsible for an enzyme activity (an esterase activity, more specifically, glycerophosphodiester phosphodiesterase activity or the like) of OBDPF protein, a polypeptide containing a portion corresponding to this region can be used.

As a region corresponding to the fifth loop of the OBDPF protein, there may be mentioned, for example, a region comprising amino acid residues of about the $206^{th}$ to $445^{th}$ in mouse SEQ ID NO: 2 and a region comprising amino acid residues of about the $205^{th}$ to $444^{th}$ in human SEQ ID NO: 4. Among them, a portion responsible for the enzyme activity is in a region comprising amino acid residues of about the $225^{th}$ to $328^{th}$ in SEQ ID NO: 2, a region comprising amino acid residues of about the $224^{th}$ to $327^{th}$ in SEQ ID NO: 4 or in a region containing a proximate part thereof.

The enzyme activity can be measured and detected using a method, for example, described in a reference (Munson et al, J. Bacteriol., vol. 175, pp. 4569–4571, 1993), using glycerophosphocoline, glycerophosphoethanol-amine, etc. as a substrate.

Remodeling process of bone is as follows [References *, ** mentioned below.]. Initially, when lining cells of osteoblastic lineage at the resting stage which covers the bone surface are exposed to bone resorbing factors, such as PTH (parathyroid hormone), etc., these cells are activated to retract, whose morphology will change from flat epithelial-like cells to rounded cells. This causes a collagen matrix layer at the bone surface to be exposed. And the activated osteoblasts secrete collagenase, which dissolves the collagen matrix layer, whereby a bone mineral layer underneath is exposed.

Subsequently, these activated osteoblasts recruit precursors of the osteoclasts (that is, pre-osteoclasts) by means of cellular or hormonal signals.

Thus, when the osteoblasts directly contact with the pre-osteoclasts, a signal of ODF (osteoclast differentiation factor) (also referred to as RANKL (Receptor activator of NF-kb ligand)) expressed on the activated osteoblasts is transduced to the pre-osteoclasts, which is then differentiated into mature osteoclasts.

Next, these osteoclasts absorb bone. Subsequently, the osteoblasts secrete matrix proteins (such as collagen, osteocalcin, etc.), to form nodule, and thereby forming a collagen woven bone, called osteoid, and then, calcification occurs on the matrix of the osteoid, to give a newly formed bone. The osteoblast which completed their mission become the lining cells again to cover the bone surface.

The protein of the present invention is specifically expressed in bone tissue, and induces morphological change of the cells (more specifically, retraction), based on its esterase activity (more specifically, glycerophosphodiester phosphodiesterase activity or the like). From this fact, it is thought that the protein of the present invention plays an important role in an activation process of the osteoblasts (lining cells of osteoblastic lineage) and induction of successive recruitment of the osteoclasts, etc. in bone remodeling.

Therefore, as the function of the protein of the present invention in the osteoblasts or in a living organism which comprises the same, in addition to the above-mentioned functions (i), (ii) and (iii), there are included functions of inducing downstream phenomena in the process of bone remodeling.

Examples of such downstream phenomena include
Secretion of collagenase from osteoblasts (*) (**)
Dissolution of collagen matrix layer at a bone surface (*) (**)
Recruitment of pre-osteoclasts (*)
Increased expression of ODF (RANKL) on the cell surface of osteoblasts (*)
Signal transduction of ODF (RANKL) (*)
Differentiation of pre-osteoclasts to mature osteoclasts (*)
Secretion of matrix proteins from osteoblasts (**)
Nodule formation by osteoblasts (**)

Further, in case of detecting a function or an activity of the protein of the present invention in osteoblasts, the above-mentioned downstream phenomena in the bone remodeling process may be detected in stead of detecting a function or an activity of the above-mentioned (i), (ii) and (iii).

REFERENCES

* Manolagas S. C., Endocrine Reviews, 21(2): 115–137, 2000
** G. Gronowicz and L. g. Raisz, Bone Formation Assays, in "Principles of Bone Biology" (J. P. Bilezikian, L. G. Raisz, G. A. Rodan, eds.) Chapter 91, pp. 1253–1265, 1996, Academic Press Inc., USA.

The protein or the polypeptide of the present invention can be produced by overexpression by means of a usual genetic recombinant technology. In addition, they can be expressed and produced in a form of a fusion protein with other protein or polypeptide.

For example, a DNA encoding the protein is inserted in a vector in a way that it is operably jointed to a downstream of an appropriate promoter, thereby constructing an expression vector. Subsequently, the obtained expression vector is introduced in a host cell.

For an expression system (host cell-vector system), for example, there may be mentioned an expression system of bacteria, yeast, insect cells and mammalian cells. Among them, in order to obtain a protein having a well-reserved function, it is preferred to use insect cells (*Spodoptera frugiperda* SF9, SF21, etc.) and mammalian cells (Monkey COS-7 cell, Chinese hamster CHO cell, human HeLa cell, etc.) as a host cell.

For a vector, in case of a mammalian cell system, retrovirus type vector, papilloma virus vector, vaccinia virus vector, SV40 type vector, etc. can be used and in case of an insect cell system, bacurovirus vector, etc. can be used.

As a promoter, in case of the mammalian cell system, SV 40 promoter, LTR promoter, elongation 1α promoter, etc. can be used and in case of the insect cell system, polyhedrin promoter, etc. can be used.

As a DNA which encodes a protein or a polypeptide, cDNA corresponding to naturally existing mRNA (for example, those having a nucleotide sequence shown by SEQ ID NO: 1 and NO: 3) can be used, but it is not limited to those. It is possible to design a DNA that corresponds to an amino acid sequence of the desired protein, and to use it. In this case, 1 to 6 kinds of codons are known to encode one amino acid, respectively. Although a selection of the codon to be used may be voluntarily decided, by considering a codon frequency in a host cell employed for expression, it is possible to design a sequence with a higher expression efficiency. A DNA having a designed sequence can be obtained through chemical synthesis of DNA, fragmentation and combination of the above-mentioned cDNA, partial modification of a nucleotide sequence, and so on. Artificial modification of the nucleotide sequence in a part or mutagenesis can be carried out by a site specific mutagenesis (Proceedings of National Academy of Sciences, vol. 81, pp. 5662–5666, 1984) etc., using a primer comprising a synthesized oligonucleotide that encodes a desired modification.

The protein or the polypeptide of the present invention can be separated and purified by optionally combining conventional purification methods (salting out using inorganic salts, fractionating precipitation using an organic solvent, ion-exchange resin column chromatography, affinity column chromatography, gel filtration method, and so on).

A nucleic acid (an oligonucleotide or a polynucleotide) which is hybridizable with the gene or the nucleic acid of the present invention under stringent condition can be used as a probe for detecting the gene of the present invention. In addition, it may be used, for example, as an antisense oligonucleotide, a ribozyme or a decoy in order to modulate gene expression or function. Examples of such a nucleic acid may include a nucleotide comprising a partial sequence of consecutive 14 bases or more, or a complementary sequence thereof in nucleotide sequences shown in SEQ ID NO: 1, NO: 3, and NO: 5 to NO: 10.

Using the protein or the polypeptide (or the gene or the nucleic acid) and the-method for detecting the function or the activity (or the expression) thereof, etc. of the present invention, substances to be tested can be studied with respect to the effect on the function or activity of the protein or the polypeptide (or the gene or the nucleic acid) of the present invention.

Through these methods, it is possible to screen or identify compounds having an effect of modulating (inhibiting or enhancing) the function or the activity (or the expression) of the protein or the polypeptide (or the gene or the nucleic acid) of the present invention. The method for screening or identifying these compounds is thought to be useful in selecting or identifying pharmaceutical compounds (for example, therapeutic or prophylactic agent for diseases relating to bone metabolism disorders), which are valuable for selling.

An effect of the test substance on an expression of the gene of the present invention can be tested as follows. For example, a vector is constructed comprising a construct in which a regulatory region (a region containing a promoter, enhancer and soon) located in the 5' upstream of the genomic DNA are connected with an appropriate reporter gene (for example, β-galactosidase gene, luciferase gene, etc.). And then, the vector is introduced into an appropriate cell. The cell is cultured in the presence of the test substance and an effect of the test substance on a gene expression is detected using an expression of the reporter gene as an index.

In addition, an effect of the test substance on the function or the activity of the protein or the polypeptide of the present invention can be detected as follows. For example, a test substance is brought in contact with cells expressing the protein or the polypeptide of the present invention, and a function or an activity of the protein or the polypeptide is detected. In comparison with a result obtained in the absence of the test substance, it can be determined whether or not the test substance has an effect of modulating the function or the activity, or a degree of the modulation effect. By using cells with no or less amount of expression of the protein or the gene of the present invention for a control, more accurate detection is possible. Further, in case of focusing on an enzyme activity (an esterase activity) as a function or an activity, isolated and purified protein or polypeptide or a part thereof of the present invention may be used in place of the cells. In this case, for example, a part containing an extracellular region, a region responsible for an enzyme activity, etc. may be used as such or in the form of a fused protein comprising these regions and other polypeptides.

From such a test result, screening, identification, evaluation, etc. can be carried out for an agent that modulates (inhibits or enhances) the function (or expression) of the protein or the polypeptide (or gene or nucleic acid) of the present invention.

When the protein of the present invention or an immunologically equivalent protein or polypeptide (synthesized polypeptide comprising a fragment of the protein or a partial sequence, etc.) is used as an antigen, an antibody can be obtained that recognizes the protein of the present invention. Immunologically equivalent protein means it causes cross reaction with an antibody for the protein of the present invention.

Polyclonal antibody can be produced by a conventional method by inoculating an antigen to a host animal (for example, rat, rabbit, etc.) and collecting an immunized serum. Monoclonal antibody can be produced by a technique such as a conventional hybridoma method. Further, by modifying the gene of the monoclonal antibody, humanized monoclonal antibody, etc. can be produced.

Using the above-obtained antibody, by an usual immunochemical method (such as enzyme immuno assay, etc.), an expression of the protein or the polypeptide of the present invention in cells or in tissues can be detected. Or else, by means of an affinity chromatography using an antibody, the protein of the present invention can be purified. Further, by using a neutralizing antibody, the function or the activity of the protein or the polypeptide of the present invention can be modulated.

Hereinbelow, the present invention will be described in more detail with reference to the following Examples, which should not be construed as limiting the scope of the present invention.

In Examples described below, each operation is conducted, unless otherwise specifically mentioned, according to a method described in "Molecular Cloning" (written by Sambrook, J., Fritsch, E. F. and Maniatis, T., published by Cold Spring Harbor Laboratory Press, 1989) or according to the instructions provided with the commercially available agents or kits.

EXAMPLES

Example 1

Isolation of cDNA of Mouse OBDPF Gene

1) Culture of Mouse Osteoblast-Like Cell Line MC3T3-E1

A mouse osteoblast-like cell line MC3T3-E1 (RIKEN RCB No.1126) was cultured as follows.

Cells (undifferentiated cells) were subcultured using α-MEM culture media (available from Gibco Co.) containing 10% bovine fetal serum. In case of having cells differentiated (matured) and calcified, the cells were cultured until confluent in the above-mentioned culture media, and ascorbic acid (0.2 mM) and β-glycerol phosphate (10 mM) were added to the culture media for inducing differentiation, and the mixture was further cultured for 11 to 14 days to obtain differentiated cells.

2) Isolation of a Gene whose Expression is Promoted at a Differentiation Stage of MC3T3-E1 into Osteoblasts From undifferentiated cells of MC3T3-El which had been cultured in the same manner as in the above 1), and from the differentiated cells (cells cultured for 11 days after addition of ascorbic acid and β-glycerol phosphate) (each about $10^9$ cells), total RNA was extracted, and mRNAs were purified using a mRNA separator kit (available from Clonetech Co.). Using the obtained mRNAs and according to differential display method (Liang et al., Science, vol. 257, pp. 967–971, 1992), candidate clones were selected as follows.

Using a reverse transcriptase and oligo (dT) primer, a single stranded cDNA was synthesized from the mRNA. Subsequently, PCR was carried out using the obtained single stranded cDNA. As the PCR primer, random primers (a primer of about 20 nucleotides size, comprising a random sequence) were used. The reaction was repeated for 4 cycles under conditions of at 95° C. for 40 seconds, at 30° C. for 1 minute, and at 72° C. for 1 minute, 30 cycles under conditions of at 95° C. for 40 seconds, at 55° C. for 1 minute, and at 72° C. for 1 minute, and for 1 cycle as the finalizing cycle, under conditions of at 72° C. for 5 minutes.

Such PCR reaction were carried out with respect to about 300 kinds of primers, and the obtained PCR products were applied to polyacrylamide gel electrophoresis, and stained with ethidium bromide. The bands developed on the gel ware observed and those identified in the sample derived from the differentiated cells and not identified in the sample derived from the undifferentiated cells were selected as candidate clones.

From the bands of the candidate clones, cDNA fragments were collected by elution, and amplified by once again carrying out PCR using the same primers. Subsequently, the amplified DNA was subcloned into a vector plasmid pGEM-T (available from Promega Co.).

3) Gene Expression in the Differentiated and Undifferentiated MC3T3-E1 Cells

Gene expression of the candidate gene in the differentiated and undifferentiated MC3T3-E1 cells were studied by Northern blotting. That is, Northern blotting was carried out using total RNA derived from the undifferentiated cells and the differentiated cells, and the cDNA fragments of the above-mentioned candidate clones as a probe. As a result, in the undifferentiated cells, no gene expression corresponding to the candidate clone was admitted, while in the differentiated cells, the expression was detected. Since the specific expression of the gene was confirmed in the differentiated cells, the candidate clone was thought to be a cDNA of a gene relating to bone metabolism.

4) Cloning of the cDNA and Determination of Nucleotide Sequence

From the mRNA derived from the differentiated cells obtained in the same manner as in the above 2), cDNA library was prepared. Using the cDNA fragments ($\alpha$-$^{32}$P-dCTP labeled) of the candidate clone obtained in the above 2) as a probe, plaque hybridization was carried out under highly stringent conditions, with respect to the above-mentioned cDNA library.

Among the positive clones, those with a longer insertion fragment was selected and with respect to plasmids derived from these clones, various kinds of deletion plasmids were prepared and nucleotide sequence of the inserted cDNA was determined by the dideoxy method. The cDNAs whose nucleotide sequences were determined were linked to obtain the whole cDNA of mouse OBDPF gene.

Through analysis on the nucleotide sequence of the cDNA, an open reading frame was identified, and then, an amino acid sequence of the protein encoded thereby was determined. The nucleotide sequence of the whole cDNA was shown in SEQ ID NO: 1, and the amino acid sequence of the OBDPF protein encoded thereby was shown in SEQ ID NO: 2 in the sequence listing mentioned below.

The molecular weight of the mouse OBDPF protein presumed from the amino acid sequence was about 61 Kd. Further, from the analysis on hydropathy of this amino acid sequence, OBDPF protein is expected to have a membrane protein like structure containing 7 transmembrane domains. It is also thought to have one leucine zipper and about eight N-glycosilation regions. Schematic drawing of the expected structure is shown in FIG. 1.

Example 2

Isolation of cDNA of Human OBDPF Gene

The fragment comprising a coding region of the whole cDNA of the mouse OBDPF gene was labeled with $\alpha$-$^{32}$P-dCTP, and using this as a probe, plaque hybridization was carried out with respect to human spleen cDNA library (available from Stratagene Co.), to obtain positive clones. Plaque hybridization was carried out under normal stringent condition.

Among the obtained positive clones, those with a longer insertion fragment was selected and with respect to plasmids derived from these clones, nucleotide sequence of the inserted cDNA was determined in the same manner as in the above examples 1–4).

Thus, the whole cDNA of the human OBDPF gene was obtained. Through analysis on the nucleotide sequence of the cDNA, an open reading frame was identified, and then, an amino acid sequence of the protein encoded thereby was determined. The nucleotide sequence of the whole cDNA was shown in SEQ ID NO: 3, and the amino acid sequence of the OBDPF protein encoded thereby was shown in SEQ ID NO: 4 in the sequence listing below.

The molecular weight of the human OBDPF protein presumed from the amino acid sequence was about 61 Kd. Further, from a comparison between the mouse and human sequences, homology between the nucleotide sequences of cDNAs of the mouse and human OBDPF genes was about 87% in the coding region (about 1.6 kb). In addition, homology between the amino acid sequences of the mouse and human OBDPF protein (539 amino acid residues) was about 87%.

Example 3

Isolation of Genomic Gene of the Mouse OBDPF

Using the whole cDNA fragment of the mouse OBDPF gene obtained in Example 1 as a probe, plaque hybridization was carried out with respect to mouse SvJ genomic library (available from Stratagene Co.), to obtain positive clones containing DNA of genomic OBDPF gene. The genomic DNA portion of these positive clones were subcloned in a vector plasmid pBluescript (available from Stratagene Co.). Subsequently, by means of Southern blotting, cDNA region (exon region) existing on a genomic DNA of each clone was determined, and nucleotide sequence of the DNA was determined by dideoxy method, with respect to the clones containing the exon region. By comparing the nucleotide sequences of the genomic DNA and the whole cDNA of the OBDPF gene, exon-intron existing region was identified.

Figure 2:
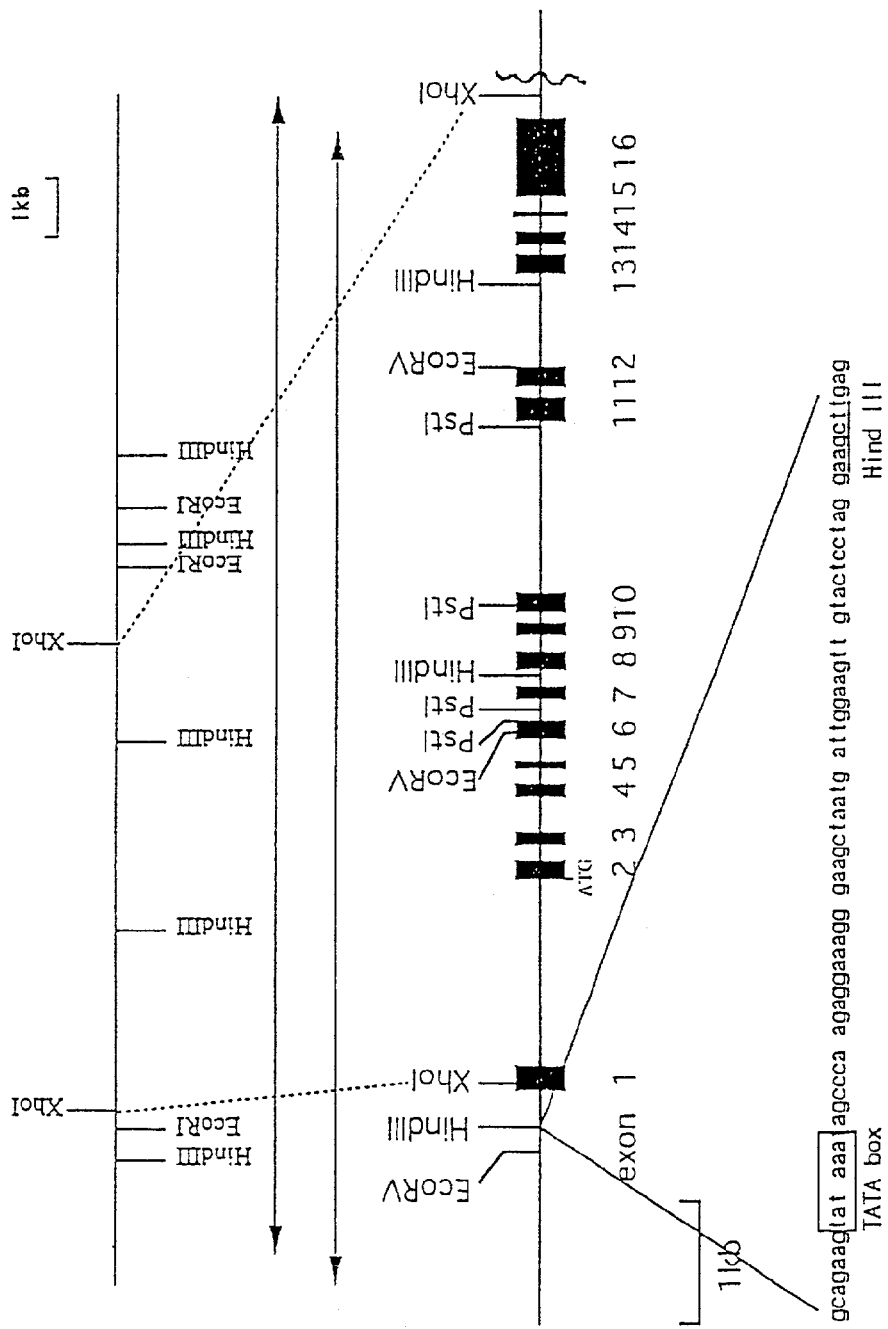
FIG. 2 is a restriction enzyme map of a mouse OBDPF genomic DNA, and a drawing showing positions of its exons. The HindIII sequence is SEQ ID NO: 17.

In SEQ ID NO: 5 to 12 of the sequence listing below, the nucleotide sequences of exon-intron boundary region of the mouse OBDPF genomic DNA were shown. Each of the SEQ ID NO: 5, NO: 6, NO: 7, NO: 8, NO: 9, NO: 10, NO: 11 and NO: 12 shows, respectively, a nucleotide sequence of exon 1, exon 2, exon 3, exon 4, exons 5 to 10, exon 11, exon 12 and exons 13 to 16, and nucleotide sequences of introns spacing at the both ends of each exon. In addition, restriction enzyme map of the mouse OBDPF genomic DNA and a location of the exons were shown in FIG. 2.

Example 4

Expression of the OBDPF Gene in a Differentiation Process of Osteoblasts

Mouse osteoblast-like cell line MC3T3-E1 was induced to differentiate by culturing the cells in a culture media to which ascorbic acid and $\beta$-glycerol phosphate were added in the same manner as in Example 1, and total RNA was prepared from the cells after 0, 4, 7, 11 and 15 days of culture. Using the Pst I fragment of the cDNA of the mouse OBDPF gene obtained in Examples 1–3) (a fragment corresponding to $662^{th}$ to $1112^{th}$ base of the SEQ ID NO: 1) as a probe, Northern blotting was carried out with respect to these total RNAs.

Figure 3:
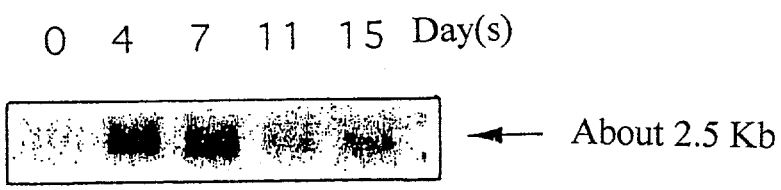
FIG. 3 is a drawing showing an expression of OBDPF gene (a result of Northern blotting) in mouse MC3T3-E1 cells induced to promote differentiation (after 0, 4, 7, 11 and 15 days of culture following addition of ascorbic acid and β-glycerol phosphate).

As a result, as shown in FIG. 3, expression of mRNA of OBDPF was hardly detected after 0 days of culture (right after confluent) (in lane 1), while significant increase in expression were observed after 4 and 7 days (in lanes 2 and 3). Beyond that, after 11 and 15 days (in lanes 4 and 5), expressions were slightly decreased, however, an expression level was still high in comparison with 0 day culture. As shown above, since the expression amount changed in accordance with a progress of differentiation (maturation) of MC3T3-E1 cells, OBDPF gene was thought to be involved in a differentiation (maturation) of the osteoblasts.

Example 5

Expression of the OBDPF Gene in Various Kinds of Tissues in Mouse

Expression pattern of the OBDPF gene in various tissues (heart, brain, spleen, lung, liver, skeletal muscle, kidney, testis, femur, and calvaria) was studied by Northern blotting as follows.

Tissues from femur and calvaria were collected from a mouse (ICR line male mouse, 12 weeks old) and poly (A)+RNA was prepared. For other tissues, commercially available mouse poly (A)+RNA (prepared from BALB/c line mouse; trade name, mouse MTN blots, available from Clonetech Co.) were used.

Northern blotting was carried out with respect to poly (A)+RNAs derived from each of the above-mentioned tissues. As a probe, Pst I fragment of cDNA of the mouse OBDPF gene obtained in Examples 1–3) (corresponding to $662^{th}$ to $1112^{th}$ nucleotide sequence of the SEQ ID NO: 1) was used.

Figure 4:
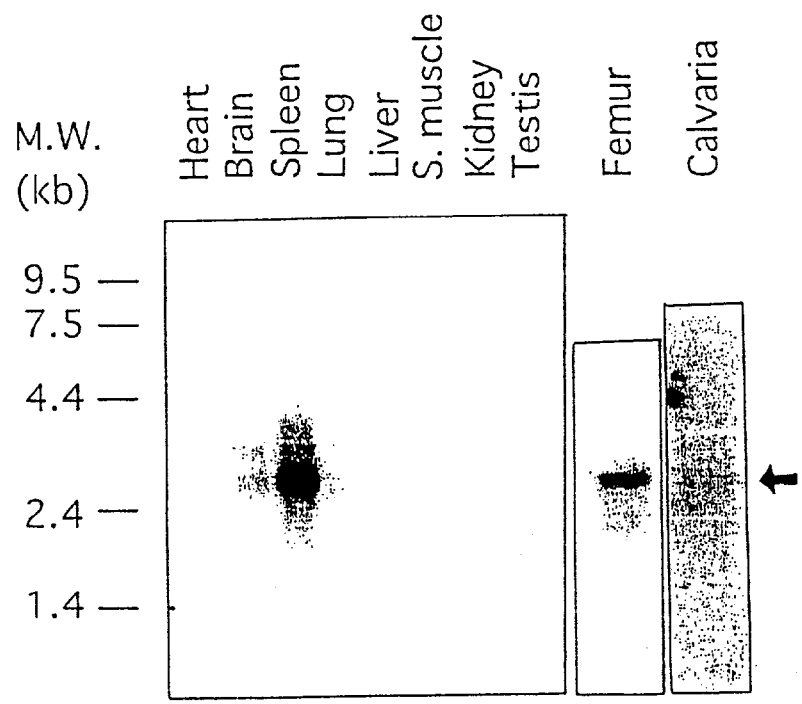
FIG. 4 is a drawing showing an expression of OBDPF gene (a result of Northern blotting) in various tissues in mouse.

As a result of the Northern blotting, as shown in FIG. 4, bands were detected of about 2.5 kb in femur, calvaria and spleen, and expressions were confirmed.

Example 6

Functional Analysis of OBDPF (I)

(Induction of Differentiation of Osteoblasts by Expression of OBDPF)

1) Construction of an OBDPF Expression Vector and Preparation of Cells Over-Expressing OBDPF A BLUNT-ENDED cDNA fragment of the mouse OBDPF gene obtained in Examples 1–3) (a fragment corresponding to from the $197^{th}$ to the 1851th base of SEQ ID NO: 1, containing entire coding region) was ligated in a vector plasmid containing elongation 1 α promoter, downstream of the above-mentioned promoter (Spe I restriction site) in a reading direction, to construct an OBDPF expression vector.

The above-obtained OBDPF expression vector was made linear by a restriction enzyme Pvu I. This was introduced into mouse osteoblast-like cell line MC3T3-E1 by means of electropolation method, and the cells were cultured in an α-MEM culture media containing neomycin (G418) for 10 days. Subsequently, 10 clones which were resistant to G418 were selected. These G418 resistant cells (that is, cells into which the expression vectors were introduced) were subjected to RT-PCR (reverse transcript-polymerase chain reaction), thereby to confirm overexpression of OBDPF mRNAs.

2) Analysis on Differentiation Marker of Osteoblasts in Cells Overexpressing OBDPF The cells overexpressing OBDPF from the above-obtained 10 clones (referred to as S01, S02, S05, S06, S07, S09, S13, S15, S17 and S18) were cultured until confluent in the culture media, andascorbic acid (0.2 mM) and β-glycerolphosphate (10 mM) were added to the culture media for inducing differentiation, and the mixture was cultured for 0 to 14 days, and then, an alkaline phosphatase activity and calcium deposition amount were measured. As a control were used cells into which vector was introduced.

The alkaline phosphatase activity was measured as follows. The cells were washed with PBS (phosphate buffered saline), and suspended in 50 mTris-HCl (pH 7.5) containing 0.1% Triton-100, and lysed ultrasonically to obtain an enzyme solution. Using a kit for measuring phosphatase activity (Phosphatase Substrate System, available from Kirkegaard & Perry Laboratories Co.), an activity was measured using p-nitrophenyl-phosphate as a substrate.

Calcium deposition amount was measured as follows. The cells were washed with PBS (phosphate buffered saline), and dissolved with 0.5N hydrochloric acid. After overnight treatment at 4° C., centrifugation was carried out to obtain a supernatant, and a calcium amount in the supernatant was measured using s kit for measuring calcium content (Calcium C Test Wako, available from Wako Junyaku Co.), according to Orthocresol phthalane Complexon method (OCPC method).

Figure 5A:
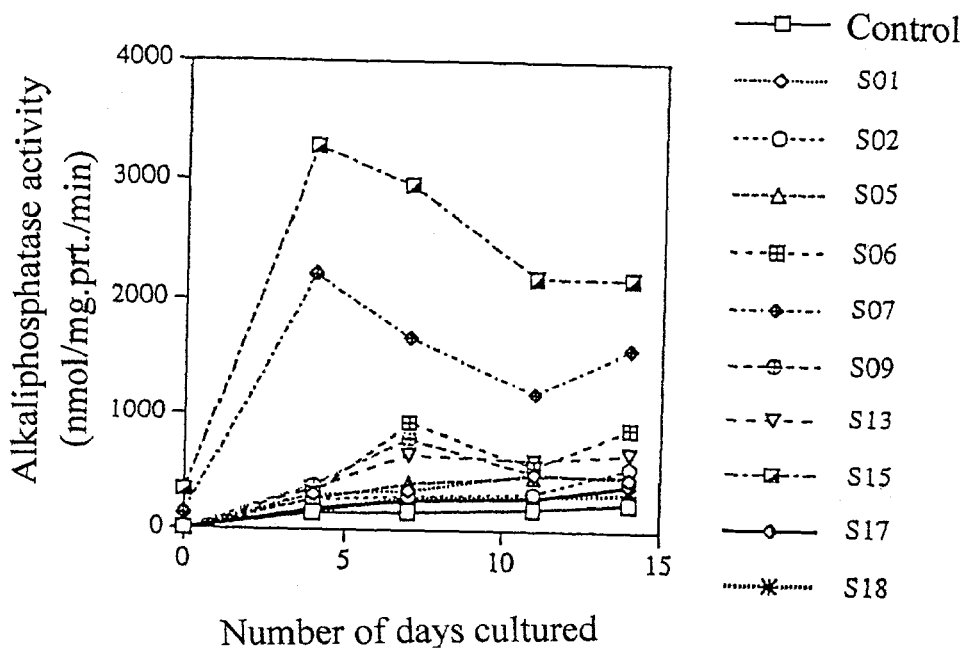
FIGS. 5A and 5B are graphs showing results of analysis of osteoblast differentiation marker in mouse MC3T3-E1 cells in which OBDPF gene is overexpressed ((A) alkaliphosphatase activity 0 to 14 days after culture, (B) amount of calcium deposited after 14 days of culture, respectively).
Figure 5B:
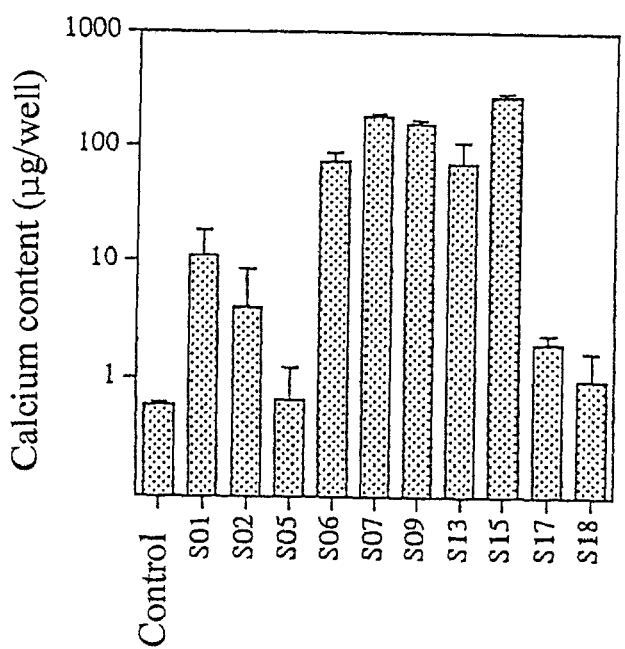

The results are shown in FIG. 5. The alkaline phosphatase activity after 0 to 14 days culture is shown in (A) and the calcium deposition amount after 14 days culture is shown in (B), respectively.

As shown in FIG. 5, in the cells overexpressing OBDPF, significant increases were confirmed in both of the alkaline phosphatase activity and the calcium deposition amount, as compared to the control cells (the cells into which vectors were introduced). Thus, since the overexpression of OBDPF resulted in a significant increase in the marker of differentiation in osteoblasts and active bone formation potential, it was concluded that OBDPF had an effect of promoting differentiation (maturation) of osteoblasts.

Example 7

Functional Analysis on OBDPF (II)

(Enzymatic Function of OBDPF and Morphological Change in Cells by OBDPF Expression)

1) Construction of a Green Fluorescent Protein (GFP) Fused OBDPF Expression Vector The cDNA fragment of OBDPF obtained in Examples 1–3) (a fragment corresponding to the $16^{th}$ to the $1821^{th}$ base of SEQ ID NO: 1; containing an entire coding region but not containing a stop codon) was ligated to Xho I and BamH I restriction sites of pEGFP-N1 (available from Clonetech Co.), in a reading direction to construct an expression vector for expressing GFP fused with OBDPF.

2) Transient Expression in 293T Cells and Staining of Actin Filament

Using Lipofection method, the above-mentioned GFP fused OBDPF expression vector was introduced into 293T cells and it was overexpressed transiently, as follows.

Specifically, $1 \times 10^5$ of 293T cells (available from Dainihon Seiyaku Co.) were inoculated onto a culture slide (available from Falcon Co.) and cultured overnight. For culture media for the 293T cells, DMEM (available from Lifetech Co.) containing 10% bovine fetal serum was used. On the following day, 3 μg of the GFP fused OBDPF expression vector (as a control, pEGFP-N1 was used in place of this vector), (which had been dissolved in 100 μl of buffer (Opti-MEM; available from Lifetech Co.) and 6 μl of an agent for Lipofection (which had been dissolved in 100 μl of Opti-MEM) were mixed, and the mixture was incubated at room temperature for 15 minutes. Subsequently, this was added dropwise to the above-mentioned cell culture liquid and the mixture was cultured overnight. After the culture liquid was removed, the cells were fixed with a neutral phosphate buffer containing 4% paraformaldehyde and 4% sucrose at room temperature for 30 minutes, and washed with phosphate buffer for 3 times. Subsequently, added thereto was 1 ml of phosphate buffer containing rhodamine-labeled phalloidin, and the mixture was incubated at room temperature for 2 hours. The resultant mixture was washed with phosphate buffer for 3 times and mounted with phosphate buffer containing 50% glycerol. Using a microscope (BX-60; available from Olimpus Co.), fluorescence was observed and photographed by a digital camera (Sensys; available from Olimpus Co.).

As a result, in the cells overexpressing the wild type GFP by introducing pEGFP-N1, the wild type GFP was present in entire cytoplasm. On the other hand, in the cells overexpressing the GFP fused OBDPF by introducing the GFP fused OBDPF expression vector, the GFP fused OBDPF was localized in the peripheral part of the cells. Additionally, the cells overexpressing the GFP fused OBDPF changed their shapes to a spherical form and actin filaments disappeared.

3) Transient Expression of a Mutant OBDPF in 293T Cells

On the $5^{th}$ loop of the OBDPF, which is an extracellular domain, there exists an amino acid sequence showing an extremely high homology with glycerophosphodiester phosphodiesterase (EC3.1.4.46) which has been reported in bacteria and yeasts.

This portion on the $5^{th}$ loop of OBDPF corresponds to, for example, the $225^{th}$ to the $328^{th}$ amino acid residues in the mouse OBDPF (SEQ ID NO: 2) and the $224^{th}$ to the $327^{th}$ amino acid residues in the human OBDPF (SEQ ID NO: 4).

Particularly, the arginine residue at the $231^{th}$ in the mouse OBDPF (the $230^{th}$ in the human OBDPF) is well conserved in *E. coli*-derived 2 kinds of glycerophosphodiester phosphodiesterase (ecUGPQ, and ecGLPQ) and the same enzyme in *Haemophilis influenzae* (hiGLPQ) (see FIG. 6), it is expected to be essential for the activity.

In order to test this assumption, a mutant of the mouse OBDPF was prepared in which the arginine residue at the $231^{st}$ was replaced with an alanine residue. Specifically, the GFP fused OBDPF expression vector, a synthesized DNA (available from Lifetech Co.), and a kit for site-directed mutagenesis (Quick Change Site-Directed Mutagenesis Kit; available from Stratagene Co.) were used to prepare a GFP fused mutant OBDPF expression vector where mutation was introduced.

(As the synthetic DNA, those having the following nucleotide sequence were used. 5'-GGG CTG GTG GGA CAC GCA GGG GCC CCC ATG CTG-3' (SEQ ID NO: 18) 5'-CAG CAT GGG GGC CCC TGC GTG TCC CAC CAG CCC-3') (SEQ ID NO: 19)

The obtained GFP fused mutant OBDPF expression vector was introduced into 293T cells by Lipofection method, and it was overexpressed transiently.

As a result, when a localization in the cell was studied, the GFP fused mutant OBDPF was localized in the peripheral part of the cell as is the case for the GFP fused OBDPF (wild type). However, with respect to the morphology of the cell, no morphological change was observed when the GFP fused mutant OBDPF was overexpressed, while those overexpressing the wild type changed their shapes to a spherical form.

4) About the Function of OBDPF

From the results of the above 1) to 3), it is expected that the OBDPF protein has an esterase activity (glycerophosphodiester phosphodiesterase activity), and a portion on the $5^{th}$ loop which is an extracellular part is responsible for this enzymatic activity.

Further, it was shown that expression of the OBDPF induced morphological change of a cell (retraction). Further, from the result of the mutagenesis, a function of inducing such morphological change (retraction) is based on the above-mentioned enzyme activity.

From the above facts and other characteristics (that is, the fact that OBDPF is expressed specifically in bone tissues, and the fact that it is expressed specifically at a differentiation stage of osteoblasts), OBDPF is thought to have a function of inducing morphological change (retraction) of the osteoblasts, particularly. In addition, there is a possibility that the OBDPF exhibits an important function of inducing adhesion of the osteoclasts to a bone surface at an initial stage of bone absorption during a bone remodeling.

The protein, the polypeptide, the gene, or the nucleic acid and the method of detecting a function or an activity thereof of the present invention are useful in elucidating a mechanism of bone metabolism, especially, differentiation of the osteoblasts and bone remodeling.

Further, they are useful in studies on pathological states, diagnostics, therapeutic and prophylactic treatment and research and development of pharmaceuticals for the diseases such as osteoporosis, osteopeterosis, osteomalacia, hypercalcemia, etc.

The invention claimed is:

1. A method of assaying a function or an activity of an osteoblast differentiation promoting factor (OBDPF) protein, said method comprising:
   culturing a cell expressing an OBDPF protein, and
   detecting a function or activity of said OBDPF protein in said cell;
   wherein said cell is an osteoblast, and said function or activity is promoting differentiation of the osteoblast to change from an immature state to a mature state;
   said OBDPF protein is a polypeptide comprising the amino acid sequence of SEQ ID NO:2 or SEQ ID NO:4, or a polypeptide encoded by a nucleic acid which hybridizes under stringent conditions with a nucleic acid comprising the nucleotide sequence of SEQ ID NO:1 or SEQ ID NO:3,
   said hybridization being carried out by conducting hybridization for 16 hours in 6×SSC or a hybridization solution having an equivalent salt concentration at a temperature of 50 to 60° C., followed by preliminary washing with 6×SSC or a solution having an equivalent salt concentration as necessary, and subsequently washing with 1×SSC or a solution having an equivalent salt concentration.

2. The method of claim 1, wherein said function or activity is detected by a marker selected from i) an amount of calcification, ii) an alkaliphosphatase activity, iii) an osteocalcin activity, and iv) an amount of expression of osteopontin.

3. A method of assaying a function or an activity of an osteoblast differentiation promoting factor (OBDPF) protein, said method comprising:
   culturing a cell expressing OBDPF protein, and
   detecting a function or activity of said OBDPF protein in said cell;
   wherein said function or activity is induction of retraction of said cell;
   said OBDPF protein is a polypeptide comprising the amino acid sequence of SEQ ID NO:2 or SEQ ID NO:4, or a polypeptide encoded by a nucleic acid which hybridizes under stringent conditions with a nucleic acid comprising the nucleotide sequence of SEQ ID NO:1 or SEQ ID NO:3;
   said hybridization being carried out by conducting hybridization for 16 hours in 6×SSC or a hybridization solution having an equivalent salt concentration at a temperature of 50 to 60° C., followed by preliminary washing with 6×SSC or a solution having an equivalent salt concentration as necessary, and subsequently washing with 1×SSC or a solution having an equivalent salt concentration.

4. The method of claim 3, wherein said cell is an osteoblast.

5. The method of claim 1 or 3, wherein said OBDPF protein is the polypeptide comprising the amino acid sequence of SEQ ID NO:2 or SEQ ID NO:4.

6. The method of claim 1 or 3, wherein said OBDPF protein is the polypeptide comprising the amino acid sequence of SEQ ID NO:4.

7. The method of claim 1 or 3, wherein said OBDPF protein is the polypeptide encoded by the nucleic acid which hybridizes under highly stringent conditions with the nucleic acid comprising the nucleotide sequence of SEQ ID NO:1 or SEQ ID NO:3.

8. The method of claim 7, wherein said OBDPF is the polypeptide encoded by the nucleic acid which hybridizes under highly stringent conditions with the nucleic acid comprising the nucleotide sequence of SEQ ID NO:3.

9. The method of claim 1 or 3, said method further comprising introducing a nucleic acid encoding said OBDPF protein into said cell expressing the OBDPF protein.

10. The method of claim 1 or 3, wherein said OBDPF protein is isolated or recombinant.

11. The method of claim 1 or 3, wherein said OBDPF protein includes an extracellular region.

* * * * *

SEQUENCE LISTING

```
<160> NUMBER OF SEQ ID NOS: 16

<210> SEQ ID NO 1
<211> LENGTH: 2457
<212> TYPE: DNA
<213> ORGANISM: Mus musculus
<220> FEATURE:
<221> NAME/KEY: CDS
<222> LOCATION: (205)..(1824)
<223> OTHER INFORMATION:
```

<400> SEQUENCE: 1

```
cccaccatga ctgtgctcga gccatagcgc ctctcccggc cttccaagag gacccacact      60
tcttcctgta ggtggcaaca gtgacacctg tttgaccagt gaggctgagc cagggactgc     120
aagagggagg aggcagacaa ctcggagagg agctgggagg cagagctgcg ggcttgcttg     180
ctcactgtgt aaaaggcctt aacc atg gca gat tcc ccc ggc tgc tgc tcc       231
                             Met Ala Asp Ser Pro Gly Cys Cys Ser
                              1               5 atc tgg gcc cgc tgc ctc cac tgc ctg tac agc tgc cac tgg agg aaa      279
Ile Trp Ala Arg Cys Leu His Cys Leu Tyr Ser Cys His Trp Arg Lys
 10              15                  20                  25 tat cct aaa cag aag atg caa acc agc aag tgc gac tgt atc tgg ttt      327
Tyr Pro Lys Gln Lys Met Gln Thr Ser Lys Cys Asp Cys Ile Trp Phe
             30                  35                  40 ggc ctg ctc ttc ctc acc ttc ctc ctg tcc ctg gga tgg ctg tac atc      375
Gly Leu Leu Phe Leu Thr Phe Leu Leu Ser Leu Gly Trp Leu Tyr Ile
         45                  50                  55 ggg ctc atc ctt ctc aat gat ctg cac aac ttc aat gaa ttc ctg ttc      423
Gly Leu Ile Leu Leu Asn Asp Leu His Asn Phe Asn Glu Phe Leu Phe
     60                  65                  70 cgc cat tgg gga cac tgg atg gac tgg tcc ctg ata gtc ctg ctg gtc      471
Arg His Trp Gly His Trp Met Asp Trp Ser Leu Ile Val Leu Leu Val
 75                  80                  85 gtc tct ctc ctg gtc aca tat gca tcc ttg cta ttg ctc ctg ggc ctg      519
Val Ser Leu Leu Val Thr Tyr Ala Ser Leu Leu Leu Leu Leu Gly Leu
 90                  95                 100                 105 ctc ctg caa ctc tgt gga cag cct ctg cat ctt cac agt ctc cac aag      567
Leu Leu Gln Leu Cys Gly Gln Pro Leu His Leu His Ser Leu His Lys
                110                 115                 120 gtg ctg ctg ctc ctc att gta ctt cta gtg gcc gcg gga ctg gtg ggc      615
Val Leu Leu Leu Leu Ile Val Leu Leu Val Ala Ala Gly Leu Val Gly
                125                 130                 135 ctg gat atc caa tgg cgg cag gag tgg cat agt tta cga ctg tca ctg      663
Leu Asp Ile Gln Trp Arg Gln Glu Trp His Ser Leu Arg Leu Ser Leu
            140                 145                 150 cag gcc aca gcc cca ttc ctt cac att gga gca gtt gct gga atc acc      711
Gln Ala Thr Ala Pro Phe Leu His Ile Gly Ala Val Ala Gly Ile Thr
        155                 160                 165 ttg ttg gcc tgg cct gtg gct gat acc ttc tac cgc atc cac cca aga      759
Leu Leu Ala Trp Pro Val Ala Asp Thr Phe Tyr Arg Ile His Pro Arg
170                 175                 180                 185 ggc ccc aag gtt ctg cta ctg ttg cta ttt ttt gga gtc act ctg gtc      807
Gly Pro Lys Val Leu Leu Leu Leu Phe Phe Gly Val Thr Leu Val
                190                 195                 200 atc tac ctg atg ccg ctg ctg ttc atc tct tcc ccc tgc atc atg aaa      855
Ile Tyr Leu Met Pro Leu Leu Phe Ile Ser Ser Pro Cys Ile Met Lys
                205                 210                 215 ctc aga gat tta ccc ccc aag cct ggg ctg gtg gga cac cga ggg gcc      903
Leu Arg Asp Leu Pro Pro Lys Pro Gly Leu Val Gly His Arg Gly Ala
            220                 225                 230 ccc atg ctg gcc cct gag aat acc ctg atg tcc ctg agg aag aca gct      951
Pro Met Leu Ala Pro Glu Asn Thr Leu Met Ser Leu Arg Lys Thr Ala
        235                 240                 245 gaa tgt gga gcg gct gtg ttt gag aca gat gtg atg gtc agc tct gac      999
Glu Cys Gly Ala Ala Val Phe Glu Thr Asp Val Met Val Ser Ser Asp
250                 255                 260                 265 gga gtc ccc ttt ctc atg cat gat gag cga ctg agc agg act acc aat     1047
Gly Val Pro Phe Leu Met His Asp Glu Arg Leu Ser Arg Thr Thr Asn
                270                 275                 280
```

-continued

| | |
|---|---|
| gta gcc tct gtg ttt cca gag cga atc tca gcc cac agc agt gac ttc<br>Val Ala Ser Val Phe Pro Glu Arg Ile Ser Ala His Ser Ser Asp Phe<br>              285                  290                          295 | 1095 |
| tcc tgg gct gaa ctg cag aga ctc aat gct gga acc tgg ttc cta gag<br>Ser Trp Ala Glu Leu Gln Arg Leu Asn Ala Gly Thr Trp Phe Leu Glu<br>       300                      305                         310 | 1143 |
| agg caa cct ttc tgg ggg gcc aaa aag ctg tca ggc tct gat cgg aag<br>Arg Gln Pro Phe Trp Gly Ala Lys Lys Leu Ser Gly Ser Asp Arg Lys<br>315                    320                        325 | 1191 |
| gag gct gag aat cag acc ata cca gca tta gaa gaa cta ctg aag gaa<br>Glu Ala Glu Asn Gln Thr Ile Pro Ala Leu Glu Glu Leu Leu Lys Glu<br>330                    335                   340                345 | 1239 |
| gca gca gct ctc aac ctt tcc atc atg ttt gac ttg cga cga ccc cca<br>Ala Ala Ala Leu Asn Leu Ser Ile Met Phe Asp Leu Arg Arg Pro Pro<br>                  350                      355                    360 | 1287 |
| aga aac cac aca tac tat gat act ttt gtg aat cag aca ctg gag gct<br>Arg Asn His Thr Tyr Tyr Asp Thr Phe Val Asn Gln Thr Leu Glu Ala<br>                     365                      370                    375 | 1335 |
| gtg ttg agt gca aac gtg tcc caa gct atg gtt ctt tgg ctc cca gat<br>Val Leu Ser Ala Asn Val Ser Gln Ala Met Val Leu Trp Leu Pro Asp<br>       380                      385                         390 | 1383 |
| gaa gac cgt gct aac gtg cag caa cgc gcc ccc aga atg cgc cag ata<br>Glu Asp Arg Ala Asn Val Gln Gln Arg Ala Pro Arg Met Arg Gln Ile<br>395                    400                        405 | 1431 |
| tat gga cat cag gga ggc aat tgg act gag agg ccc cag ttt ctc aac<br>Tyr Gly His Gln Gly Gly Asn Trp Thr Glu Arg Pro Gln Phe Leu Asn<br>410                    415                   420                425 | 1479 |
| ctc ccc tat caa gac ctg cca gca ttg gat atc aag gcc ctg cac cag<br>Leu Pro Tyr Gln Asp Leu Pro Ala Leu Asp Ile Lys Ala Leu His Gln<br>                  430                      435                    440 | 1527 |
| gat aat atc tca gtg aac ctg ttt gta gtg aac aag ccc tgg ctc ttc<br>Asp Asn Ile Ser Val Asn Leu Phe Val Val Asn Lys Pro Trp Leu Phe<br>                     445                      450                    455 | 1575 |
| tcc ctg ctc tgg tgt gca ggg gtg gat tct gtc acc acc aat gcc tgc<br>Ser Leu Leu Trp Cys Ala Gly Val Asp Ser Val Thr Thr Asn Ala Cys<br>       460                      465                         470 | 1623 |
| cag ctg ctg caa cag atg cag aac ccc ctc tgg ctt ctt ccc cct caa<br>Gln Leu Leu Gln Gln Met Gln Asn Pro Leu Trp Leu Leu Pro Pro Gln<br>475                    480                   485 | 1671 |
| aaa tac tta atg att tgg gtg atc acc gac tgt gcc tcc att ctg ctg<br>Lys Tyr Leu Met Ile Trp Val Ile Thr Asp Cys Ala Ser Ile Leu Leu<br>490                    495                   500                505 | 1719 |
| ctt ttg agt atc ttc ctc ctc cga ggg gga tgt gct aag aga aac aga<br>Leu Leu Ser Ile Phe Leu Leu Arg Gly Gly Cys Ala Lys Arg Asn Arg<br>                  510                      515                520 | 1767 |
| aca ggc tta gaa aca gca gtg cta ctg acc aag atc aac aat ttc gcc<br>Thr Gly Leu Glu Thr Ala Val Leu Leu Thr Lys Ile Asn Asn Phe Ala<br>                     525                      530                    535 | 1815 |
| tct gag tga atgccgggcc caggccgcca ccagctgctg tctaaggcct<br>Ser Glu | 1864 |
| gtgtgcactg ttcaaaggga aggacaggag ctgaagtgga atgtcctaga atcaaatgtt | 1924 |
| tggaggaggg agcattgcta acagaagatt ttgaactcag agggccctct gtccagatgg | 1984 |
| tgggcatgtc tcaagctgcc atggaatttg ctgcctttgg tgtttgacat gaattagtcg | 2044 |
| gaaagacagt gactgacaag aagttactcc caaaatgaaa ttaaagcaag gaagtgagag | 2104 |
| agattgccaa gataatgcat taggcttgtg tgcacatgta cttggataga agaagcaggg | 2164 |
| tgtgtcaggg tgggatagct cagaatgatg actgaaggaa atttgccac aatggccttt | 2224 |

-continued

```
ccggaagaac tcttaagatg ctgaagacag tccacactcc atgccttctc ttctcaccct    2284
cacacttcat cttcttttct gcctacaggc tgggagtgaa aaagctcatt tagcaatata    2344
atattgtgtc tatggtaggt ttttgttgtg agcaatgaat ggttcctgta tcttgcctgt    2404
taatctgtta ttcaatgaat tttttaatttg tcatttgaaa aaaaaaaaaa aaa          2457
```

<210> SEQ ID NO 2
<211> LENGTH: 539
<212> TYPE: PRT
<213> ORGANISM: Mus musculus

<400> SEQUENCE: 2

```
Met Ala Asp Ser Pro Gly Cys Cys Ser Ile Trp Ala Arg Cys Leu His
1               5                   10                  15

Cys Leu Tyr Ser Cys His Trp Arg Lys Tyr Pro Lys Gln Lys Met Gln
            20                  25                  30

Thr Ser Lys Cys Asp Cys Ile Trp Phe Gly Leu Leu Phe Leu Thr Phe
        35                  40                  45

Leu Leu Ser Leu Gly Trp Leu Tyr Ile Gly Leu Ile Leu Leu Asn Asp
    50                  55                  60

Leu His Asn Phe Asn Glu Phe Leu Phe Arg His Trp Gly His Trp Met
65                  70                  75                  80

Asp Trp Ser Leu Ile Val Leu Leu Val Val Ser Leu Leu Val Thr Tyr
                85                  90                  95

Ala Ser Leu Leu Leu Leu Leu Gly Leu Leu Leu Gln Leu Cys Gly Gln
            100                 105                 110

Pro Leu His Leu His Ser Leu His Lys Val Leu Leu Leu Leu Ile Val
        115                 120                 125

Leu Leu Val Ala Ala Gly Leu Val Gly Leu Asp Ile Gln Trp Arg Gln
    130                 135                 140

Glu Trp His Ser Leu Arg Leu Ser Leu Gln Ala Thr Ala Pro Phe Leu
145                 150                 155                 160

His Ile Gly Ala Val Ala Gly Ile Thr Leu Leu Ala Trp Pro Val Ala
                165                 170                 175

Asp Thr Phe Tyr Arg Ile His Pro Arg Gly Pro Lys Val Leu Leu Leu
            180                 185                 190

Leu Leu Phe Phe Gly Val Thr Leu Val Ile Tyr Leu Met Pro Leu Leu
        195                 200                 205

Phe Ile Ser Ser Pro Cys Ile Met Lys Leu Arg Asp Leu Pro Pro Lys
    210                 215                 220

Pro Gly Leu Val Gly His Arg Gly Ala Pro Met Leu Ala Pro Glu Asn
225                 230                 235                 240

Thr Leu Met Ser Leu Arg Lys Thr Ala Glu Cys Gly Ala Ala Val Phe
                245                 250                 255

Glu Thr Asp Val Met Val Ser Ser Asp Gly Val Pro Phe Leu Met His
            260                 265                 270

Asp Glu Arg Leu Ser Arg Thr Thr Asn Val Ala Ser Val Phe Pro Glu
        275                 280                 285

Arg Ile Ser Ala His Ser Ser Asp Phe Ser Trp Ala Glu Leu Gln Arg
    290                 295                 300

Leu Asn Ala Gly Thr Trp Phe Leu Glu Arg Gln Pro Phe Trp Gly Ala
305                 310                 315                 320

Lys Lys Leu Ser Gly Ser Asp Arg Lys Glu Ala Glu Asn Gln Thr Ile
                325                 330                 335
```

-continued

```
Pro Ala Leu Glu Glu Leu Leu Lys Glu Ala Ala Ala Leu Asn Leu Ser
        340                 345                 350

Ile Met Phe Asp Leu Arg Arg Pro Arg Asn His Thr Tyr Tyr Asp
            355                 360                 365

Thr Phe Val Asn Gln Thr Leu Glu Ala Val Leu Ser Ala Asn Val Ser
        370                 375                 380

Gln Ala Met Val Leu Trp Leu Pro Asp Glu Asp Arg Ala Asn Val Gln
385                 390                 395                 400

Gln Arg Ala Pro Arg Met Arg Gln Ile Tyr Gly His Gln Gly Gly Asn
                405                 410                 415

Trp Thr Glu Arg Pro Gln Phe Leu Asn Leu Pro Tyr Gln Asp Leu Pro
            420                 425                 430

Ala Leu Asp Ile Lys Ala Leu His Gln Asp Asn Ile Ser Val Asn Leu
        435                 440                 445

Phe Val Val Asn Lys Pro Trp Leu Phe Ser Leu Leu Trp Cys Ala Gly
    450                 455                 460

Val Asp Ser Val Thr Thr Asn Ala Cys Gln Leu Leu Gln Gln Met Gln
465                 470                 475                 480

Asn Pro Leu Trp Leu Leu Pro Pro Gln Lys Tyr Leu Met Ile Trp Val
                485                 490                 495

Ile Thr Asp Cys Ala Ser Ile Leu Leu Leu Ser Ile Phe Leu Leu
            500                 505                 510

Arg Gly Gly Cys Ala Lys Arg Asn Arg Thr Gly Leu Glu Thr Ala Val
        515                 520                 525

Leu Leu Thr Lys Ile Asn Asn Phe Ala Ser Glu
    530                 535
```

<210> SEQ ID NO 3
<211> LENGTH: 2199
<212> TYPE: DNA
<213> ORGANISM: Homo sapiens
<220> FEATURE:
<221> NAME/KEY: CDS
<222> LOCATION: (252)..(1871)
<223> OTHER INFORMATION:

<400> SEQUENCE: 3

```
gcagatttgc tctccctccc gcttcctccc tcccatcttc ccacccgggc tgtgcccagg     60
ccacagagca gctgcaggcc ttgggagagg acccacacag cctcctgtag gtggcaacag    120
tgccacctgt ttgactcata gggctgaacc gaggactgaa aaagggagga ggcagaccac    180
tcggagagga gctgggaagc agtgcagaga ggagagcgga gcggagctgc cgctgagcaa    240
aggccttcac c atg gcc gag tcc ccc ggc tgc tgc tcc gtc tgg gcc cgc    290
            Met Ala Glu Ser Pro Gly Cys Cys Ser Val Trp Ala Arg
              1               5                  10 tgc ctc cac tgc ctg tat agc tgc cac tgg agg aaa tgc ccc aga gag    338
Cys Leu His Cys Leu Tyr Ser Cys His Trp Arg Lys Cys Pro Arg Glu
         15                  20                  25 agg atg caa acc agc aag tgc gac tgt atc tgg ttt ggc ctg ctc ttc    386
Arg Met Gln Thr Ser Lys Cys Asp Cys Ile Trp Phe Gly Leu Leu Phe
 30                  35                  40                  45 ctc acc ttc ctc ctt tcc ctg agc tgg ctg tac atc ggg ctc gtc ctt    434
Leu Thr Phe Leu Leu Ser Leu Ser Trp Leu Tyr Ile Gly Leu Val Leu
             50                  55                  60 ctc aat gac ctg cac aac ttc aat gaa ttc ctc ttc cgc cgc tgg gga    482
Leu Asn Asp Leu His Asn Phe Asn Glu Phe Leu Phe Arg Arg Trp Gly
         65                  70                  75
```

```
cac tgg atg gac tgg tcc ctg gca ttc ctg ctg gtc atc tct cta ctg     530
His Trp Met Asp Trp Ser Leu Ala Phe Leu Leu Val Ile Ser Leu Leu
        80                  85                  90 gtc aca tat gca tcc ttg cta ttg gtc ctg gcc ctg ctc ctg cgg ctt     578
Val Thr Tyr Ala Ser Leu Leu Leu Val Leu Ala Leu Leu Leu Arg Leu
    95                  100                 105 tgt aga cag ccc ctg cat ctg cac agc ctc cac aag gtg ctg ctg ctc     626
Cys Arg Gln Pro Leu His Leu His Ser Leu His Lys Val Leu Leu Leu
110                 115                 120                 125 ctc att atg ctg ctt gtg gcg gct ggc ctt gtg gga ctg gac atc caa     674
Leu Ile Met Leu Leu Val Ala Ala Gly Leu Val Gly Leu Asp Ile Gln
                130                 135                 140 tgg cag cag gag tgg cat agc ttg cgt gtg tca ctg cag gcc aca gcc     722
Trp Gln Gln Glu Trp His Ser Leu Arg Val Ser Leu Gln Ala Thr Ala
            145                 150                 155 cca ttc ctt cat att gga gca gcc gct gga att gcc ctc ctg gcc tgg     770
Pro Phe Leu His Ile Gly Ala Ala Ala Gly Ile Ala Leu Leu Ala Trp
        160                 165                 170 cct gtg gct gat acc ttc tac cgt atc cac cga aga ggt ccc aag att     818
Pro Val Ala Asp Thr Phe Tyr Arg Ile His Arg Arg Gly Pro Lys Ile
    175                 180                 185 ctg cta ctg ctc cta ttt ttt gga gtt gtc ctg gtc atc tac ttg gcc     866
Leu Leu Leu Leu Leu Phe Phe Gly Val Val Leu Val Ile Tyr Leu Ala
190                 195                 200                 205 ccc cta tgc atc tcc tca ccc tgc atc atg gaa ccc aga gac tta cca     914
Pro Leu Cys Ile Ser Ser Pro Cys Ile Met Glu Pro Arg Asp Leu Pro
                210                 215                 220 ccc aag cct ggg ctg gtg gga cac cga ggg gcc ccc atg ctg gct ccc     962
Pro Lys Pro Gly Leu Val Gly His Arg Gly Ala Pro Met Leu Ala Pro
            225                 230                 235 gag aac acc ctg atg tcc ttg cgg aag aca gct gaa tgc gga gct act    1010
Glu Asn Thr Leu Met Ser Leu Arg Lys Thr Ala Glu Cys Gly Ala Thr
        240                 245                 250 gtg ttt gag act gat gtg atg gtc agc tcc gat ggg gtc ccc ttc ctc    1058
Val Phe Glu Thr Asp Val Met Val Ser Ser Asp Gly Val Pro Phe Leu
    255                 260                 265 atg cat gat gag cac ctc agc agg acc acg aat gta gcc tct gta ttc    1106
Met His Asp Glu His Leu Ser Arg Thr Thr Asn Val Ala Ser Val Phe
270                 275                 280                 285 cca acc cga atc aca gcc cac agc agt gac ttc tcc tgg act gaa ctg    1154
Pro Thr Arg Ile Thr Ala His Ser Ser Asp Phe Ser Trp Thr Glu Leu
                290                 295                 300 aag aga ctc aat gct gga tcc tgg ttc cta gag agg cga ccc ttc tgg    1202
Lys Arg Leu Asn Ala Gly Ser Trp Phe Leu Glu Arg Arg Pro Phe Trp
            305                 310                 315 ggg gcc aaa ccg ctg gca ggc cct gat cag aaa gag gct gag agt cag    1250
Gly Ala Lys Pro Leu Ala Gly Pro Asp Gln Lys Glu Ala Glu Ser Gln
        320                 325                 330 acg gta cca gca tta gaa gag cta ttg gag gaa gct gca gcc ctc aac    1298
Thr Val Pro Ala Leu Glu Glu Leu Leu Glu Glu Ala Ala Ala Leu Asn
    335                 340                 345 ctt tcc atc atg ttc gac ttg cgc cga ccc cca cag aac cac aca tac    1346
Leu Ser Ile Met Phe Asp Leu Arg Arg Pro Pro Gln Asn His Thr Tyr
350                 355                 360                 365 tat gac act ttt gtg atc cag aca ttg gag act gtg ctg aat gca agg    1394
Tyr Asp Thr Phe Val Ile Gln Thr Leu Glu Thr Val Leu Asn Ala Arg
                370                 375                 380 gtg ccc caa gcc atg gtc ttt tgg cta cca gat gaa gat cgg gct aat    1442
Val Pro Gln Ala Met Val Phe Trp Leu Pro Asp Glu Asp Arg Ala Asn
            385                 390                 395
```

-continued

| | | |
|---|---|---|
| gtc caa cga cgg gca cct gga atg cgc cag ata tat gga cgt cag gga<br>Val Gln Arg Arg Ala Pro Gly Met Arg Gln Ile Tyr Gly Arg Gln Gly<br>      400                          405                          410 | 1490 |

```
gtc caa cga cgg gca cct gga atg cgc cag ata tat gga cgt cag gga   1490
Val Gln Arg Arg Ala Pro Gly Met Arg Gln Ile Tyr Gly Arg Gln Gly
            400                 405                 410 ggc aac aga acg gag agg ccc cag ttt ctt aac ctc ccc tat caa gat   1538
Gly Asn Arg Thr Glu Arg Pro Gln Phe Leu Asn Leu Pro Tyr Gln Asp
        415                 420                 425 ctg cca cta ttg gat atc aag gca ttg cat aag gat aat gtc tcg gtg   1586
Leu Pro Leu Leu Asp Ile Lys Ala Leu His Lys Asp Asn Val Ser Val
430                 435                 440                 445 aac cta ttt gta gtg aac aag ccc tgg ctc ttc tct ctg ctt tgg tgt   1634
Asn Leu Phe Val Val Asn Lys Pro Trp Leu Phe Ser Leu Leu Trp Cys
                450                 455                 460 gca ggg gtg gat tcg gtc acc acc aac gac tgc cag ctg ctg cag cag   1682
Ala Gly Val Asp Ser Val Thr Thr Asn Asp Cys Gln Leu Leu Gln Gln
            465                 470                 475 atg cgt tac cct atc tgg ctt att acc cct caa acc tac cta atc ata   1730
Met Arg Tyr Pro Ile Trp Leu Ile Thr Pro Gln Thr Tyr Leu Ile Ile
        480                 485                 490 tgg gtc att acc aat tgt gtt tcc acc atg ctg ctt ttg tgg acc ttc   1778
Trp Val Ile Thr Asn Cys Val Ser Thr Met Leu Leu Leu Trp Thr Phe
    495                 500                 505 ctc ctc caa agg aga ttt gtt aag aag aga ggg aaa act ggc tta gaa   1826
Leu Leu Gln Arg Arg Phe Val Lys Lys Arg Gly Lys Thr Gly Leu Glu
510                 515                 520                 525 aca gca gtg ctg ctg aca agg atc aac aat ttc atg atg gag tga       1871
Thr Ala Val Leu Leu Thr Arg Ile Asn Asn Phe Met Met Glu
                530                 535 atgccctgcc ctgcttcccc acccaagcca gtctacattg cccaaacagc aagggttgga 1931 gagtggctta agtggaatgc ttcaggggtg gtgggttgca agtgggggga gctttgccaa 1991 caggaggttt tgaaccatga gggccctctg cccaggtgat gggcattccc taagctgcta 2051 tggaatctgc tccctttggg gttttgacct gagatgtttg ggaagagagt gagtaatgag 2111 aagtttctcc tcaaatgaaa ctagaacaga ggaagtaaaa gggagattgc tcggaaaaaa 2171 aaaaaaaaaa aaaaaaaaaa aaaaaaaa                                   2199
```

<210> SEQ ID NO 4
<211> LENGTH: 539
<212> TYPE: PRT
<213> ORGANISM: Homo sapiens

<400> SEQUENCE: 4

```
Met Ala Glu Ser Pro Gly Cys Cys Ser Val Trp Ala Arg Cys Leu His
  1               5                  10                  15

Cys Leu Tyr Ser Cys His Trp Arg Lys Cys Pro Arg Glu Arg Met Gln
             20                  25                  30

Thr Ser Lys Cys Asp Cys Ile Trp Phe Gly Leu Leu Phe Leu Thr Phe
         35                  40                  45

Leu Leu Ser Leu Ser Trp Leu Tyr Ile Gly Leu Val Leu Leu Asn Asp
     50                  55                  60

Leu His Asn Phe Asn Glu Phe Leu Phe Arg Arg Trp Gly His Trp Met
 65                  70                  75                  80

Asp Trp Ser Leu Ala Phe Leu Leu Val Ile Ser Leu Leu Val Thr Tyr
                 85                  90                  95

Ala Ser Leu Leu Leu Val Leu Ala Leu Leu Leu Arg Leu Cys Arg Gln
            100                 105                 110

Pro Leu His Leu His Ser Leu His Lys Val Leu Leu Leu Leu Ile Met
        115                 120                 125
```

```
Leu Leu Val Ala Ala Gly Leu Val Gly Leu Asp Ile Gln Trp Gln Gln
    130             135             140

Glu Trp His Ser Leu Arg Val Ser Leu Gln Ala Thr Ala Pro Phe Leu
145             150             155             160

His Ile Gly Ala Ala Ala Gly Ile Ala Leu Leu Ala Trp Pro Val Ala
                165             170             175

Asp Thr Phe Tyr Arg Ile His Arg Arg Gly Pro Lys Ile Leu Leu Leu
            180             185             190

Leu Leu Phe Phe Gly Val Val Leu Val Ile Tyr Leu Ala Pro Leu Cys
        195             200             205

Ile Ser Ser Pro Cys Ile Met Glu Pro Arg Asp Leu Pro Pro Lys Pro
210             215             220

Gly Leu Val Gly His Arg Gly Ala Pro Met Leu Ala Pro Glu Asn Thr
225             230             235             240

Leu Met Ser Leu Arg Lys Thr Ala Glu Cys Gly Ala Thr Val Phe Glu
            245             250             255

Thr Asp Val Met Val Ser Ser Asp Gly Val Pro Phe Leu Met His Asp
            260             265             270

Glu His Leu Ser Arg Thr Thr Asn Val Ala Ser Val Phe Pro Thr Arg
    275             280             285

Ile Thr Ala His Ser Ser Asp Phe Ser Trp Thr Glu Leu Lys Arg Leu
    290             295             300

Asn Ala Gly Ser Trp Phe Leu Glu Arg Arg Pro Phe Trp Gly Ala Lys
305             310             315             320

Pro Leu Ala Gly Pro Asp Gln Lys Glu Ala Glu Ser Gln Thr Val Pro
            325             330             335

Ala Leu Glu Glu Leu Leu Glu Glu Ala Ala Ala Leu Asn Leu Ser Ile
            340             345             350

Met Phe Asp Leu Arg Arg Pro Pro Gln Asn His Thr Tyr Tyr Asp Thr
            355             360             365

Phe Val Ile Gln Thr Leu Glu Thr Val Leu Asn Ala Arg Val Pro Gln
    370             375             380

Ala Met Val Phe Trp Leu Pro Asp Glu Asp Arg Ala Asn Val Gln Arg
385             390             395             400

Arg Ala Pro Gly Met Arg Gln Ile Tyr Gly Arg Gln Gly Gly Asn Arg
            405             410             415

Thr Glu Arg Pro Gln Phe Leu Asn Leu Pro Tyr Gln Asp Leu Pro Leu
            420             425             430

Leu Asp Ile Lys Ala Leu His Lys Asp Asn Val Ser Val Asn Leu Phe
        435             440             445

Val Val Asn Lys Pro Trp Leu Phe Ser Leu Leu Trp Cys Ala Gly Val
    450             455             460

Asp Ser Val Thr Thr Asn Asp Cys Gln Leu Leu Gln Gln Met Arg Tyr
465             470             475             480

Pro Ile Trp Leu Ile Thr Pro Gln Thr Tyr Leu Ile Ile Trp Val Ile
            485             490             495

Thr Asn Cys Val Ser Thr Met Leu Leu Leu Trp Thr Phe Leu Leu Gln
            500             505             510

Arg Arg Phe Val Lys Lys Arg Gly Lys Thr Gly Leu Glu Thr Ala Val
            515             520             525

Leu Leu Thr Arg Ile Asn Asn Phe Met Met Glu
    530             535
```

```
<210> SEQ ID NO 5
<211> LENGTH: 2529
<212> TYPE: DNA
<213> ORGANISM: Mus musculus
<220> FEATURE:
<221> NAME/KEY: exon
<222> LOCATION: (2314)..(2508)
<223> OTHER INFORMATION: Genomic DNA (exon 1)

<400> SEQUENCE: 5
tgatgcccac ttctggctta caggcatata tgtagttaga acactgtata catatgtctt      60
agtcagggtt tctattcctg cacaaacatc atgaccaaga agcaagttgg ggcagaaagg     120
gtttattcgg cctatacttc catactgcag ttcatcacca aggaagtcag gactggaact     180
caagcaggtc aggaagcagg agctgatgca gaggccatgg agggatgtta cttactggct     240
tgcttcccct ggcttgccca gcctgctcag ttatagaacc aagactacca gcccagagat     300
ggtcccaccc acaaggggtc tttcccccctt aatcactaat tgagaaagtg ccttacagat     360
ggatctcatg gaggcatttt ctcaactgaa gctcctttct ctgtgataac tccagctgtg     420
tcaagttgac acaaaactag ccagtacaac atagtaaaca atctttttta aaaaatgtt      480
caaggtcctt agcctgtact ttgcatataa gaaaatcaag tgtctgcttt accatacaat     540
agcaaatact tgagagatgg agttgtctgg agaatgtgtt taatttagct catggtgttg     600
gaggccctgg gccatgctta gaaacccata ttagttcatg acagaagtac gatggagcag     660
gatggaagaa aatagtggaa ggatctgggt cccatcacca gccttcgaga gcatactctc     720
cagtatacaa aagacagaca ctccacgaga acctacctcg ctataaagtt tcccccaacc     780
tcccaaattg taccacaggc cagggaacaa gctgtgaaca cacaagccct tggggaacat     840
taaatatcta acagagatag taccgtggta caaagaggtg gttatataga gttacaatgt     900
cagtgaatat tagagctggg aacagaagcc agttacattt accatatagt tctttctagt     960
gccctgcaat cctactaatg cttttccgtt tacagaacaa aactactgcc cccttgcttt    1020
ctcccttaaa aaggaagtgg gggtgggggg ggacaaggat tattccttac cttatgccag    1080
atttcttgtc tccagttaga agccagaagg ggggccagcc atgcagtacc tcatacaggc    1140
tatatttgaa acctttgggg agttttcaag ccttgaggct catccatgca tatcgaatgc    1200
tgtccccacc ccaccacccc ctaaaaggct ctcaaaccat ccccacgtac aagaaaacaa    1260
gactctagaa tccaccacaa cccaagcaaa ggaaattgaa aaacaacctg ccaagaatga    1320
ctcccagtgg aggactaggt gacccgctgg ccctcccctgg cttcctgcca gcaagcagcc    1380
ttgcttctct ttgcattttta attctgagag agttagagaa tctctgtcat gccaaatag     1440
agcctctgga tacaatggga aagctgagag ggagggaacc agctcctggc agaagagagc    1500
cagtctccct cactggataa aattgagtgt gtggagggggg agggaagcc agcttatctg    1560
taaggagtca tcctttccca ccctccatag tgctcacaca cagaccccaa gtcacttcat    1620
cagccccaat ccaagagctg tccatcaaca cagcgcccat gcaatcctgt acttttata     1680
ctaagctgac cacagcttgc atggccacct gcttctttttg tacatgttca tcttccaaaa    1740
gcctggtacc ctaatacact atacactcct gaagccattc agtgcttgat aaacaagaca    1800
gtgagcctga tatcctgaat gagcacctga tgggtggtgc ggtgagggct attgaataca    1860
tccacaggga ctcctggtcc agaaatgggg catctactgc ctagagttca taaagtcact    1920
tcaatagcat cactacgatg gaattgcaga agtataaata gcccaagagg aaagggaagc    1980
taatgattgg aagttgtact cctaggaagc ttgaggttag acttccttat ccactcaaga    2040
```

```
gtttctaggg gactggcagg gcccttctc ctcgctgcca agttgcaaaa ttgtgtggtc    2100
acctccccca gcttccctcc ctcctatgcc ctcagtcctg gcctcctaga gccaggacaa    2160
agccctcagg cagtgactgg gaggggaaca ggaggaggga cagagggatg gggaaggctg    2220
cacaaaggaa ttcctcacac caagcccct gactgccagc tccagagagt aaagaagccg     2280
acctcctctc cagctagctc actcgctcat ctt ccc acc atg act gtg ctc gag    2334
                                    Pro Thr Met Thr Val Leu Glu
                                      1               5 cca tag cgc ctc tcc cgg cct tcc aag agg acc cac act tct tcc tgt    2382
Pro     Arg Leu Ser Arg Pro Ser Lys Arg Thr His Thr Ser Ser Cys
             10                  15                  20 agg tgg caa cag tga cac ctg ttt gac cag tga ggc tga gcc agg gac    2430
Arg Trp Gln Gln     His Leu Phe Asp Gln     Gly     Ala Arg Asp
     25                      30                          35 tgc aag agg gag gag gca gac aac tcg gag agg agc tgg gag gca gag    2478
Cys Lys Arg Glu Glu Ala Asp Asn Ser Glu Arg Ser Trp Glu Ala Glu
             40                  45                  50 ctg cgg gct tgc ttg ctc act gtg taa aag gtgtgagggc tcgggaaagc t    2529
Leu Arg Ala Cys Leu Leu Thr Val     Lys
         55                      60

<210> SEQ ID NO 6
<211> LENGTH: 158
<212> TYPE: DNA
<213> ORGANISM: Mus musculus
<220> FEATURE:
<221> NAME/KEY: exon
<222> LOCATION: (21)..(134)
<223> OTHER INFORMATION: Genomic DNA (exon 2)

<400> SEQUENCE: 6
caaatgtcct tttcccccag gcc tta acc atg gca gat tcc ccc ggc tgc tgc     53
                         Ala Leu Thr Met Ala Asp Ser Pro Gly Cys Cys
                          1               5                  10 tcc atc tgg gcc cgt tgc ctc cac tgc ctg tac agc tgc cac tgg agg     101
Ser Ile Trp Ala Arg Cys Leu His Cys Leu Tyr Ser Cys His Trp Arg
         15                  20                  25 aaa tat cct aaa cag aag atg caa acc agc aag gtggagaaag gatgggggg    154
Lys Tyr Pro Lys Gln Lys Met Gln Thr Ser Lys
         30                  35 tgac                                                                158

<210> SEQ ID NO 7
<211> LENGTH: 159
<212> TYPE: DNA
<213> ORGANISM: Mus musculus
<220> FEATURE:
<221> NAME/KEY: exon
<222> LOCATION: (32)..(136)
<223> OTHER INFORMATION: Genomic DNA (exon 3)

<400> SEQUENCE: 7
agctgagagc ttctctcctg ctcctttgca g tgc gac tgt atc tgg ttt ggc      52
                                 Cys Asp Cys Ile Trp Phe Gly
                                  1               5 ctg ctc ttc ctc acc ttc ctc ctg tcc ctg gga tgg ctg tac atc ggg    100
Leu Leu Phe Leu Thr Phe Leu Leu Ser Leu Gly Trp Leu Tyr Ile Gly
         10                  15                  20 ctc atc ctt ctc aat gat ctg cac aac ttc aat gag tgtgtcatgt          146
Leu Ile Leu Leu Asn Asp Leu His Asn Phe Asn Glu
         25                  30                  35 accacctcct tcc                                                      159
```

<210> SEQ ID NO 8
<211> LENGTH: 155
<212> TYPE: DNA
<213> ORGANISM: Mus musculus
<220> FEATURE:
<221> NAME/KEY: exon
<222> LOCATION: (26)..(119)
<223> OTHER INFORMATION: Genomic DNA (exon 4)

<400> SEQUENCE: 8

```
aacatcttcc tttaccctcc tacag att cct gtt ccg cca ttg ggg aca ctg      52
                            Ile Pro Val Pro Pro Leu Gly Thr Leu
                              1               5 gat gga ctg gtc cct gat agt cct gct ggt cgt ctc tct cct ggt cac     100
Asp Gly Leu Val Pro Asp Ser Pro Ala Gly Arg Leu Ser Pro Gly His
 10              15                  20                  25 ata tgc atc ctt gct att g gttggtccag ggacatccgg cctaactccc acataa   155
Ile Cys Ile Leu Ala Ile
                30
```

<210> SEQ ID NO 9
<211> LENGTH: 1552
<212> TYPE: DNA
<213> ORGANISM: Mus musculus
<220> FEATURE:
<221> NAME/KEY: exon
<222> LOCATION: (26)..(85)
<223> OTHER INFORMATION: Genomic DNA (exon 5)
<220> FEATURE:
<221> NAME/KEY: exon
<222> LOCATION: (328)..(426)
<223> OTHER INFORMATION: Genomic DNA (exon 6)
<220> FEATURE:
<221> NAME/KEY: exon
<222> LOCATION: (600)..(693)
<223> OTHER INFORMATION: Genomic DNA (exon 7)
<220> FEATURE:
<221> NAME/KEY: exon
<222> LOCATION: (853)..(1001)
<223> OTHER INFORMATION: Genomic DNA (exon 8)
<220> FEATURE:
<221> NAME/KEY: exon
<222> LOCATION: (1124)..(1206)
<223> OTHER INFORMATION: Genomic DNA (exon 9)
<220> FEATURE:
<221> NAME/KEY: exon
<222> LOCATION: (1318)..(1468)
<223> OTHER INFORMATION: Genomic DNA (exon 10)

<400> SEQUENCE: 9

```
aagtgcccct tctgtctgtt cccag ctc ctg ggc ctg ctc ctg caa ctc tgt      52
                            Leu Leu Gly Leu Leu Leu Gln Leu Cys
                              1               5 gga cag cct ctg cat ctt cac agt ctc cac aag gtacagtgaa ttggcagtga   105
Gly Gln Pro Leu His Leu His Ser Leu His Lys
 10              15                  20 tgaggagagg ggatgctggg tccagcaccc tgatggtcat ttgcttttct atccctgggg   165
tcaagatcag gacctgaaat ccagtacatg tttattgagt gaaagcatag tacatgcgtt   225
caggaagggg aagaatcctg tgtccacaga atgaagaggg agccccagtc accatgagcc   285
taggctaaca aggaaggccc attcattcgt ccctggcccc ag gtg ctg ctg ctc      339
                                                Val Leu Leu Leu ctc att gta ctt cta gtg gcc gcg gga ctg gtg ggc ctg gat atc caa     387
Leu Ile Val Leu Leu Val Ala Ala Gly Leu Val Gly Leu Asp Ile Gln
 25                  30                  35                  40 tgg cgg cag gag tgg cat agt tta cga ctg tca ctg cag gtgagtagct      436
Trp Arg Gln Glu Trp His Ser Leu Arg Leu Ser Leu Gln
                 45                  50
```

```
gacctccact atctatgtgg gagccttggc ccatgcctat tctggaacat gacattgcct      496
cctggtccta tgagactgca gatctctctg gactgcagag aaggggagg cacaacacag       556 aacaatagga agaagagcct tcctcaccag ctcttttcca cag gcc aca gcc cca        611
                                                Ala Thr Ala Pro
                                                 55 ttc ctt cac att gga gca gtt gct gga atc acc ttg ttg gcc tgg cct        659
Phe Leu His Ile Gly Ala Val Ala Gly Ile Thr Leu Leu Ala Trp Pro
        60                  65                  70 gtg gct gat acc ttc tac cgc atc cac cca aga g gtgccaacat               703
Val Ala Asp Thr Phe Tyr Arg Ile His Pro Arg
 75                  80 cagcccacat tcactctcac tggacaccag tgtctctgcc acccacccca ccccacccc       763 agtttcctgt acctgagctc tgccctctgc ccgtagagct ccaccttacc tgttgccttt      823
cccctaagct tgtcctccac tttctacag gc  ccc aag gtt ctg cta ctg ttg        875
                                    Gly Pro Lys Val Leu Leu Leu Leu
                                                         90 cta ttt ttt gga gtc act ctg gtc atc tac ctg atg ccg ctg ctg ttc        923
Leu Phe Phe Gly Val Thr Leu Val Ile Tyr Leu Met Pro Leu Leu Phe
    95                  100                 105 atc tct tcc ccc tgc atc atg aaa ctc aga gat tta ccc ccc aag cct        971
Ile Ser Ser Pro Cys Ile Met Lys Leu Arg Asp Leu Pro Pro Lys Pro
        110                 115                 120 ggg ctg gtg gga cac cga ggg gcc ccc atg gtaagtggtg ggcagaaatc         1021
Gly Leu Val Gly His Arg Gly Ala Pro Met
125                 130 tagacaagtg aaaatgaatt tgctcctcta ggcttcagga tcaggtctga ggttcccagc     1081
cccgcccttc cctgctacct tctcaccacc tcctttcac ag ctg gcc cct gag         1135
                                              Leu Ala Pro Glu
                                                         135 aat acc ctg atg tcc ctg agg aag aca gct gaa tgt gga gcg gct gtg       1183
Asn Thr Leu Met Ser Leu Arg Lys Thr Ala Glu Cys Gly Ala Ala Val
    140                 145                 150 ttt gag aca gat gtg atg gtc ag  gtgatggagg gtgggaccta ggggttggt       1236
Phe Glu Thr Asp Val Met Val Ser
155                 160 gggctggggg acacagtggg gggactcggg aaaagatgtc agctccagag ctttgtcccc     1296
tgacacttct tgtgcccaca g c tct gac gga gtc ccc ttt ctc atg cat gat     1348
                         Ser Asp Gly Val Pro Phe Leu Met His Asp
                                     165                 170 gag cga ctg agc agg act acc aat gta gcc tct gtg ttt cca gag cga       1396
Glu Arg Leu Ser Arg Thr Thr Asn Val Ala Ser Val Phe Pro Glu Arg
        175                 180                 185 atc tca gcc cac agc agt gac ttc tcc tgg gct gaa ctg cag aga ctc       1444
Ile Ser Ala His Ser Ser Asp Phe Ser Trp Ala Glu Leu Gln Arg Leu
        190                 195                 200 aat gct gga acc tgg ttc cta gag gtgaggacgc cagccaagat gaggccacta      1498
Asn Ala Gly Thr Trp Phe Leu Glu
205                 210 cctccttgac actcagggca gagtccattt cagcagtatg cactcgctgc accc           1552

<210> SEQ ID NO 10
<211> LENGTH: 358
<212> TYPE: DNA
<213> ORGANISM: Mus musculus
<220> FEATURE:
<221> NAME/KEY: exon
<222> LOCATION: (116)..(337)
<223> OTHER INFORMATION: Genomic DNA (exon 11)
```

<400> SEQUENCE: 10

```
ctgcagagca aattccaggc cagacaggac tgtagaaaac aaacaaacag atggcaagga      60
ttgggagaaa accttgaggc ctcttgtgat gttgaaataa tttcctctct tatag agg     118
                                                                Arg
                                                                  1 caa cct ttc tgg ggg gcc aaa aag ctg tca ggc tct gat cgg aag gag      166
Gln Pro Phe Trp Gly Ala Lys Lys Leu Ser Gly Ser Asp Arg Lys Glu
          5                  10                  15 gct gag aat cag acc ata cca gca tta gaa gaa cta ctg aag gaa gca      214
Ala Glu Asn Gln Thr Ile Pro Ala Leu Glu Glu Leu Leu Lys Glu Ala
     20                  25                  30 gca gct ctc aac ctt tcc atc atg ttt gac ttg cgc cga ccc cca aga      262
Ala Ala Leu Asn Leu Ser Ile Met Phe Asp Leu Arg Arg Pro Pro Arg
 35                  40                  45 aac cac aca tac tat gat act ttt gtg aat cag aca ctg gag gct gtg      310
Asn His Thr Tyr Tyr Asp Thr Phe Val Asn Gln Thr Leu Glu Ala Val
 50              55                  60                  65 ttg agt gca aac gtg tcc caa gct atg gtgatgtatc caggctccta a         358
Leu Ser Ala Asn Val Ser Gln Ala Met
                 70
```

<210> SEQ ID NO 11
<211> LENGTH: 234
<212> TYPE: DNA
<213> ORGANISM: Mus musculus
<220> FEATURE:
<221> NAME/KEY: exon
<222> LOCATION: (33)..(181)
<223> OTHER INFORMATION: Genomic DNA (exon 12)

<400> SEQUENCE: 11

```
attaaatttt gttcattgcc cctgaaccac ag gtt ctt tgg ctc cca gat gaa      53
                                    Val Leu Trp Leu Pro Asp Glu
                                      1               5 gac cgt gct aac gtg cag caa cgc gcc ccc aga atg cgc cag ata tat     101
Asp Arg Ala Asn Val Gln Gln Arg Ala Pro Arg Met Arg Gln Ile Tyr
             10                  15                  20 gga cat cag gga ggc aat tgg act gag agg ccc cag ttt ctc aac ctc     149
Gly His Gln Gly Gly Asn Trp Thr Glu Arg Pro Gln Phe Leu Asn Leu
         25                  30                  35 ccc tat caa gac ctg cca gca ttg gat atc aa gtgagtgtca aggaaaggaa    201
Pro Tyr Gln Asp Leu Pro Ala Leu Asp Ile
 40                  45 taaaaggacc ccccaaggtt gactgtcaga aaa                                234
```

<210> SEQ ID NO 12
<211> LENGTH: 1582
<212> TYPE: DNA
<213> ORGANISM: Mus musculus
<220> FEATURE:
<221> NAME/KEY: exon
<222> LOCATION: (62)..(209)
<223> OTHER INFORMATION: Genomic DNA (exon 13)
<220> FEATURE:
<221> NAME/KEY: exon
<222> LOCATION: (348)..(430)
<223> OTHER INFORMATION: Genomic DNA (exon 14)
<220> FEATURE:
<221> NAME/KEY: exon
<222> LOCATION: (714)..(739)
<223> OTHER INFORMATION: Genomic DNA (exon 15)
<220> FEATURE:
<221> NAME/KEY: exon
<222> LOCATION: (827)..(1496)
<223> OTHER INFORMATION: Genomic DNA (exon 16)

<400> SEQUENCE: 12

```
gagtctcaga cgtgagctgg gcaaattctg tatgttcctc catttccccc cacttccaca      60 g ggc cct gca cca gga taa tat ctc agt gaa cct gtt tgt agt gaa caa     109
  Gly Pro Ala Pro Gly     Tyr Leu Ser Glu Pro Val Cys Ser Glu Gln
  1               5                    10                      15 gcc ctg gct ctt ctc cct gct ctg gtg tgc agg ggt gga ttc tgt cac       157
Ala Leu Ala Leu Leu Pro Ala Leu Val Cys Arg Gly Gly Phe Cys His
                20                  25                  30 cac caa tgc ctg cca gct gct gca aca gat gca gaa ccc cct ctg gct       205
His Gln Cys Leu Pro Ala Ala Ala Thr Asp Ala Glu Pro Pro Leu Ala
            35                  40                  45 tct t gtaaggactc tagaactgtc cctgcccctc atgtccaatc tcttatttcc          259
Ser tcttaaacct gtacccctcc atatttattt accccatatg ctactcttgg gagttctggc     319
cactgaaggg acttttccat ttccatag cc  ccc tca aaa ata ctt aat gat        370
                                   Ser Pro Ser Lys Ile Leu Asn Asp
                                       50                  55 ttg ggt gat cac cga ctg tgc ctc cat tct gct gct ttt gag tat ctt       418
Leu Gly Asp His Arg Leu Cys Leu His Ser Ala Ala Phe Glu Tyr Leu
            60                  65                  70 cct cct ccg agg gtgagtgctt ttgccttggt ctcctgggca ctttcccggg           470
Pro Pro Pro Arg
            75 ccccaagtaa aaaaggttga gtctgactgg agtgcactgc ccgggattaa gattttgtca     530 ttgcaaattt cgagttttcc ttatctctat aaaatgtctt gaccctggcg aaagcagttt     590 tggggaaccc tgggttggag agtcttgtaa caagttggtg gaacttgcaa cagaaaaaaa     650 gaaagtctca atctctctct ctctctttct ctctctctct ttctctcccc ccccctctc      710 tag ggg atg tgc taa gag aaa cag aac ag  gtaagaatgc ccttgccctt         759
    Gly Met Cys     Glu Lys Gln Asn Arg
                80 cctttcttat tttctcctca tttccctgg cttcactccc tgtatgaccc gtctcttact      819 tctctag g ctt aga aac agc agt gct act gac caa gat caa caa ttt cgc    869
          Leu Arg Asn Ser Ser Ala Thr Asp Gln Asp Gln Gln Phe Arg
              85                  90                  95 ctc tga gtg aat gcc ggg ccc agg ccg cca cca gct gct gtc taa ggc       917
Leu     Val Asn Ala Gly Pro Arg Pro Pro Ala Ala Val     Gly
            100                 105                 110 ctg tgt gca ctg ttc aaa ggg aag gac agg agc tga agt gga atg tcc       965
Leu Cys Ala Leu Phe Lys Gly Lys Asp Arg Ser     Ser Gly Met Ser
        115                 120                     125 tag aat caa atg ttt gga gga ggg agc att gct aac aga aga ttt tga      1013
    Asn Gln Met Phe Gly Gly Gly Ser Ile Ala Asn Arg Arg Phe
        130                 135                 140 act cag agg gcc ctc tgt cca gat ggt ggg cat gtc tca agc tgc cat      1061
Thr Gln Arg Ala Leu Cys Pro Asp Gly Gly His Val Ser Ser Cys His
            145                 150                 155 gga att tgc tgc ctt tgg tgt ttg aca tga att agt cgg aaa gac agt      1109
Gly Ile Cys Cys Leu Trp Cys Leu Thr     Ile Ser Arg Lys Asp Ser
            160                 165                     170 gac tga caa gaa gtt act ccc aaa atg aaa tta aag caa gga agt gag      1157
Asp     Gln Glu Val Thr Pro Lys Met Lys Leu Lys Gln Gly Ser Glu
            175                 180                 185 aga gat tgc caa gat aat gca tta ggc ttg tgt gca cat gta ctt gga      1205
Arg Asp Cys Gln Asp Asn Ala Leu Gly Leu Cys Ala His Val Leu Gly
            190                 195                 200
```

| | | | | | | | | | | | | | | | |
|---|---|---|---|---|---|---|---|---|---|---|---|---|---|---|---|
| tag | aag | aag | cag | ggt | gtg | tca | ggg | tgg | gat | agc | tca | gaa | tga | tga | ctg | 1253 |
| | Lys | Lys | Gln | Gly | Val | Ser | Gly | Trp | Asp | Ser | Ser | Glu | | | Leu |
| | 205 | | | | | 210 | | | | | 215 | | | | |

| aag | gaa | att | tgg | cca | caa | tgg | cct | ttc | cgg | aag | aac | tct | taa | gat | gct | 1301 |
| Lys | Glu | Ile | Trp | Pro | Gln | Trp | Pro | Phe | Arg | Lys | Asn | Ser | | Asp | Ala |
| | | | 220 | | | | 225 | | | | | | | 230 | |

| gaa | gac | agt | cca | cac | tcc | atg | cct | tct | ctc | acc | ctc | aca | ctt | cat | 1349 |
| Glu | Asp | Ser | Pro | His | Ser | Met | Pro | Ser | Leu | Leu | Thr | Leu | Thr | Leu | His |
| | | | 235 | | | | | 240 | | | | | 245 | | |

| ctt | ctt | ttc | tgc | cta | cag | gct | ggg | agt | gaa | aaa | gct | cat | tta | gca | ata | 1397 |
| Leu | Leu | Phe | Cys | Leu | Gln | Ala | Gly | Ser | Glu | Lys | Ala | His | Leu | Ala | Ile |
| | | 250 | | | | | 255 | | | | | 260 | | | |

| taa | tat | tgt | gtc | tat | ggt | agg | ttt | ttg | ttg | tga | gca | atg | aat | ggt | tcc | 1445 |
| | Tyr | Cys | Val | Tyr | Gly | Arg | Phe | Leu | Leu | | Ala | Met | Asn | Gly | Ser |
| | | 265 | | | | 270 | | | | | | 275 | | | |

| tgt | atc | ttg | cct | gtt | aat | ctg | tta | ttc | aat | gaa | ttt | tta | att | tgt | cat | 1493 |
| Cys | Ile | Leu | Pro | Val | Asn | Leu | Leu | Phe | Asn | Glu | Phe | Leu | Ile | Cys | His |
| | | 280 | | | | | 285 | | | | | 290 | | | | ttg gtcacagtct aatcatttct gtgccggagt tggaagaatg cttttccat   1546
Leu ctggaactgg atgtaaaatg acattgagag gtcatc   1582

<210> SEQ ID NO 13
<211> LENGTH: 54
<212> TYPE: PRT
<213> ORGANISM: Mus musculus

<400> SEQUENCE: 13

Val Gly His Arg Gly Ala Pro Met Leu Ala Pro Glu Asn Thr Leu Met
1               5                   10                  15

Ser Leu Arg Lys Thr Ala Glu Cys Gly Ala Ala Val Phe Glu Thr Asp
                20                  25                  30

Val Met Val Ser Ser Asp Gly Val Pro Phe Leu Met His Asp Glu Arg
            35                  40                  45

Leu Ser Arg Thr Thr Asn
        50

<210> SEQ ID NO 14
<211> LENGTH: 54
<212> TYPE: PRT
<213> ORGANISM: Mus musculus

<400> SEQUENCE: 14

Val Ala His Arg Gly Gly Gly Lys Leu Ala Pro Glu Asn Thr Leu Ala
1               5                   10                  15

Ser Ile Asp Val Gly Ala Lys Tyr Gly His Lys Met Ile Glu Phe Asp
                20                  25                  30

Ala Lys Leu Ser Lys Asp Gly Glu Ile Phe Leu Leu His Asp Asp Asn
            35                  40                  45

Leu Glu Arg Thr Ser Asn
        50

<210> SEQ ID NO 15
<211> LENGTH: 54
<212> TYPE: PRT
<213> ORGANISM: Mus musculus

```
-continued

<400> SEQUENCE: 15

Ile Ala His Arg Gly Ala Ser Gly Tyr Leu Pro Glu His Thr Leu Pro
1               5                   10                  15

Ala Lys Ala Met Ala Tyr Ala Gln Gly Ala Asp Tyr Leu Glu Gln Asp
            20                  25                  30

Leu Val Met Thr Lys Asp Asp Asn Leu Val Val Leu His Asp His Tyr
        35                  40                  45

Leu Asp Arg Val Thr Asp
    50

<210> SEQ ID NO 16
<211> LENGTH: 54
<212> TYPE: PRT
<213> ORGANISM: Mus musculus

<400> SEQUENCE: 16

Ile Ala His Arg Gly Ala Ser Gly Tyr Leu Pro Glu His Thr Leu Glu
1               5                   10                  15

Ser Lys Ala Leu Ala Phe Ala Gln His Ser Asp Tyr Leu Glu Gln Asp
            20                  25                  30

Leu Ala Met Thr Lys Asp Gly Arg Leu Val Val Ile His Asp His Phe
        35                  40                  45

Leu Asp Gly Leu Thr Asp
    50
```